(12) United States Patent
Elliott et al.

(10) Patent No.: US 7,217,689 B1
(45) Date of Patent: May 15, 2007

(54) GLYCOSYLATION ANALOGS OF ERYTHROPOIETIN

(75) Inventors: Steven G. Elliott, Newbury Park, CA (US); Thomas E. Byrne, Arlington, VA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/479,892

(22) Filed: Jun. 6, 1995

Related U.S. Application Data

(63) Continuation of application No. 08/108,016, filed on Aug. 17, 1993, now abandoned, which is a continuation of application No. 07/942,126, filed on Sep. 8, 1992, now abandoned, which is a continuation of application No. 07/594,448, filed on Oct. 12, 1990, which is a continuation of application No. 07/421,444, filed on Oct. 13, 1989, now abandoned.

(51) Int. Cl.
*A61K 38/18* (2006.01)
*C07K 14/505* (2006.01)
*C12N 15/18* (2006.01)
*C12N 15/63* (2006.01)
*C12N 15/85* (2006.01)

(52) U.S. Cl. .................... 514/8; 514/12; 530/397; 536/23.51; 435/320.1; 435/325

(58) Field of Classification Search .............. 514/8; 435/240.2, 252.11; 530/395, 397; 536/23.5, 536/23.51; 930/90
See application file for complete search history.

(56) References Cited

U.S. PATENT DOCUMENTS

| | | | |
|---|---|---|---|
| 4,397,840 A | 8/1983 | Takezawa et al. | |
| 4,667,016 A | 5/1987 | Lai ............................. | 530/397 |
| 4,703,008 A | 10/1987 | Lin ............................ | 435/240.2 |
| 5,041,376 A | 8/1991 | Gething et al. .......... | 435/172.3 |
| 5,217,881 A * | 6/1993 | Park ........................ | 435/69.52 |
| 5,218,092 A * | 6/1993 | Sasaki et al. ............ | 435/69.51 |

FOREIGN PATENT DOCUMENTS

| | | |
|---|---|---|
| AU | 90/59145 | 1/1991 |
| AU | A-59145/90 | 1/1991 |
| EP | 0 148 605 A2 | 7/1985 |
| EP | 148605 | 7/1985 |
| EP | 0 267 678 A1 | 5/1988 |
| EP | 267678 | 5/1988 |
| EP | 0 357 804 A1 | 3/1990 |
| EP | 357804 | 3/1990 |
| EP | 0 370 205 B1 | 5/1990 |
| EP | 370205 | 5/1990 |
| EP | 0 428 267 A2 | 5/1991 |
| EP | 428267 | 5/1991 |
| EP | 0 640 619 B1 | 7/1997 |
| WO | WO 89/03840 | 5/1989 |
| WO | 90/14363 | 11/1990 |
| WO | WO 90/14363 | 11/1990 |
| WO | WO 00/24893 | 5/2000 |

OTHER PUBLICATIONS

Rudinger In "Peptide Hormones" (Jun. 1976) ed. J.A. Parsons, University Park Press, Baltimore pp. 1-7.*
Ashwell et al. Methods Enzymol. 50, 287-288 (1978).
Boissel et al. in The Biology of Hematopoiesis pp. 227-232 (1990).
Boissel et al. J. Biol. Chem. 268, 15983-15993 (1993).
Bradford Anal. Biochem. 72, 248-254 (1976).
Briggs et al. Am. J. Physiol. 227, 1385-1388 (1974).
Chern et al. Eur. J. Biochem. 202, 225-229 (1991).
Delorme et al. Biochemistry 31, 9871-9876 (1992).
Dube et al. J. Biol. Chem. 263, 17516-17521 (1988).
Elliott et al. Abstract of Presentation at Keystone Symposium, Mar. 21-27, 1992.
Elliott et al. J. Cell. Biochem. Supp. 15G, Abstract No. R215 (1991).
Elliott et al. J. Cell Biochem. Supp. 17B, Abstract No. E318 (1993).
Kessler et al. J. Biol. Chem. 254, 7901-7908 (1979).
Lin et al. in Molecular and Cellular Aspects of Erythropoietin & Erythropoiesis, I.N. Rich., ed., Springer-Verlag, Berlin 12-36 (1987).
Pierce et al. Ann. Rev. Biochem. 50, 465-495 (1981).
Yamaguchi et al. J. Biol. Chem. 266, 20434-20439 (1991).
Gavel et al. (1990), *Protein Engineering*, 3(5):433-442.
Shakin-Eshleman (1996), *Trends in Glycoscience and Glycotechnology*, 8(40):115-130.
Chou and Fasman (1978), *Adv. Enzymol.*, 47:45-148.
Garnier et al. (1978), *J. Mol. Biol.*, 120:97-120.
Lim (1974), *J. Mol. Biol.*, 88:873-894.
Burbaum et al. (1990) *Proteins* 7:99-111.
Kyngas et al. (1998), *Protein Engineering*, 11(5):345-348.
Gallagher et al. (1988), *J. Cell Biology*, 107:2059-2073.
Dordal et al. (1985), *Endocrinology*, 116(6):2293-2299.
Dube et al. (1988), *J. Biol. Chem.*, 263(33):17516-17521.
Watowich et al. (1994), *Molecular and Cellular Biology*, 14(6):3535-3549.
Ashwell et al., "A Protein from Mammalian Liver That Specifically Binds Galactose-Terminated Glycoproteins", *Methods Enzymol.* 50:287-288 1978).
Boissel et al., "Erythropoietin Structure-Function Relationships", *The Biology of Hematopoiesis* pp. 227-232 (1990).
Boissel et al., "Erythropoietin Structure-Function Relationships", *J. Biol. Chem.* 268:15983-15993 (1993).
Bradford, "A Rapid and Sensitive Method for the Quantitation of Microgram Quantities of Protein Utilizing the Principle of Protein-Dye Binding", *Anal. Biochem.* 72:248-254 (1976.
Briggs et al., "Hepatic clearance of intact and desialylated erythropoietin", *Am. J. Physiol.* 227:1385-1388 (1974).
Broudy et al., "Recombinant Human Erythropoietin: Purification and Analysis of Carbohydrate Linkage", *Arch. Biochem. Biophys.* 265:329-336 (1988).

(Continued)

Primary Examiner—Robert C. Hayes
(74) *Attorney, Agent, or Firm*—Marshall, Gerstein & Borun LLP

(57) ABSTRACT

Erythropoietin analogs having at least one additional site for glycosylation, or a rearrangement of at least one site for glycosylation are disclosed. The invention also relates to DNA sequences encoding said erythropoietin analogs, and recombinant plasmids and host cells for analog expression.

40 Claims, 19 Drawing Sheets

OTHER PUBLICATIONS

Burnette, "Western Blotting: Electrophoretic Transfer of Proteins from Sodium Dodecyl Sulfate-Polyacrylamide Gels to Unmodified Nitrocellulose and Radiographic Detection with Antibody and Radioiodinated Protein A", *Anal. Biochem.* 112:195-203 (1981).

Chern et al., "Structural role of amino acids 99-110 in recombinant human erythropoietin", *Eur. J. Biochem.* 202:225-229 (1991).

Cheetham et al. "NMR Structure of Human Erythropoietin and a Comparison with its Receptor Bound Conformation," *Nature* 5(10):861-866.

Cotes et al., "Bio-assay of Erythropoietin in Mice Made Polycythaemic by Exposure to Air at a Reduced Pressure", *Nature* 191:1065-1067 (1961).

Davis et al., "Characterization of Recombinant Human Erythropoietin Produced in Chinese Hamster Ovary Cells", *Biochemistry* 26:2633-2638 (1987).

Delorme et al., "Role of Glycosylation on the Secretion and Biological Activity of Erythropoietin", *Biochemistry* 31:9871-9876 (1992).

Dorado et al., "Electrophoretic Behavior of Erythropoietin in Polyacrylamide Gel", *Biochem. Medicine* 6:238-245 (1972).

Dordal et al., "The Role of Carbohydrate in Erythropoietin Action", *Endocrinology* 116:2293-2299 (1985).

Dube et al., "Glycosylation at Specific Sites of Erythropoietin is Essential for Biosynthesis, Secretion, and Biological Function", *J. Biol. Chem.* 263:17516-17521 (1988).

Egrie et al., "Characterization and Biological Effects of Recombinant Human Erythropoietin", *Immunobiology* 172:213-224 (1986).

Egrie et al., "Pharmacokinetics of Recombinant Human Erythropoietin (rHeEpo) Administered to Hemodialysis (HD) Patients," *Kidney Intl.* 33:262 (1988).

Egrie et al. (1997), *Blood* 90(1):56A, Abstract 243.I.

Elliott et al., "Structural Requirements for O-Linked Glycosylation of Human Erythropoietin", Abstract of Presentation at Keystone Symposium, Mar. 21-27, 1992

Elliott et al., "Structural Requirements for O-Linked Glycosylation of Human Erythropoietin", Abstracts of the Protein Society, 5th Symp, Abstract No. M43 (1991).

Elliott et al., "Characterization of Anti Erythropoietin Monoclonal Antibodies", *Blood* 74(Supp. 1):A 1228 (1989).

Elliott et al., "Secretion of glycosylated human erythropoietin from yeast directed by the α—factor leader region", *Gene* 79:167-180 (1989).

Elliott et al. , "An Immunological Approach to Determination of Protein Structure: Human Erythropoietin", *J. Cell. Biochem.* Supp. 15G, Abstract No. R215 (1991).

Elliott et al., "Effect of Disulfide Bonds on the Structure and Activity of Erythropoietin", *J. Cell. Biochem.* Supp. 17B, Abstract No. E318 (1993).

Emini et al. "Induction of Hepatitis A Virus-Neutralizing Antibody by a Virus-Specific Synthetic Peptide," *J. Virology* 55(3):836-839.

Fu, et al. (1993), "The sheep erythropoietin gene: molecular cloning and effect of hemorrhage on plasma erythropoietin and renal/liver messenger RNA in adult sheep," *Molecular and Cellular Endocrinology* 93:107-116.

Fuhr et al., "Evaluation of Commercial Erythropoietin Activity after Preparative Isoelectric Focusing", *Biochem. Biophys. Res. Comm.* 98:930-935 (1981).

Fukuda et al., "Survival of Recombinant Erythropoietin in the Circulation: The Role of Carbohydrates", *Blood* 73:84-89 (1989).

Fukuda et al. (1990), "Structure and Role of Carbohydrate in Human Erythropoietin," *Adv. Exp. Med. Biol.* 271:53-68.

Goldwasser et al., "On the Mechanism of Erythropoietin-induced Differentiation", *J. Biol. Chem.* 249:4202-4206 (1974).

Holmes et al., "A Rapid Boiling Method for the Preparation of Bacterial Plasmids", *Anal. Biochem.* 117:193-197 (1981).

Imai et al. (1990), "Physicochemical and biological characterization of asialoerythropoietin," *Eur. J. Biochem.* 194:457-462.

Iscove et al., "Erythroid Colony Formation in Cultures of Mouse and Human Bone Marrow Analysis of the Requirement for Erythropoietin by Gel Filtration and Affinity Chromatography on Agarose-Concanavalin A", *J. Cell Physiol.* 83:309-320 (1974).

Jacobs et al. (1985), "Isolation and characterization of genomic and cDNA clones of human erythropoietin," *Nature* 313:806-810.

Kessler et al., "Structures of N-Glycosidic Carbohydrate Unites of Human chorionic Gonadotropin", *J. Biol. Chem.* 254:7901-7908 (1979).

Krystal et al. (1986), "Purification of Human Erythropoietin to Homogeneity by a Rapid Five-Step Procedure," *Blood* 67:71-79.

Kunkel et al., "Rapid and Efficient Site-Specific Mutagenesis without Phenotypic selection", *Methods Enzymol* 154:367-382 (1987).

Lai et al., "Structural Characterization of Human Erythropoietin", *J. Biol. Chem.* 261:3116-3121 (1986).

Law et al., "Chromosomal assignment of the human erythropoietin gene and its DNA polymorphism", *Proc. Natl. Acad. Sci. USA* 83:6920-6924 (1986).

Lee et al., "Alteration of Terminal Glycosylation Sequences on N-Linked Oligosaccharides of Chinese Hamster Ovary Cells by Expression of β-Galactoside a2, 6-Sialyltransferase", *J. Biol. Chem.* 264:13848-13855 (1989).

Lin, "The Molecular Biology of Erythropoietin", Molecular and Cellular Aspects of Erythropoietin & Erythropoiesis, I.N. Rich., ed., Springer-Verlag, Berlin 23-36 (1987).

Lin et al., "Cloning and expression of the human erythropoietin gene", *Proc. Natl. Acad. Sci. USA* 82:7580-7584 (1985).

Lowy et al., "Inactivation of Erythropoietin by Neuraminidase and by Mild Substitution Reactions", *Nature* 185:102-103 (1960).

Lukowsky et al., "Studies on the Role of Sialic Acid in the Physical and Biological Proeprties of Erythropoietin", *Can. J. Biochem.* 50:909-917 (1972).

Messing, "New M13 Vectors for Cloning", *Methods Enzymol.* 101:20-78 (1983).

Miyake et al., "Purification of Human Erythropoietin", *J. Biol. Chem.*, 252:5558-5564 (1977).

Morrell et al., "Physical and Chemical Studies on Ceruloplasmin", *J. Biol. Chem.* 243:155-159 (1968).

Mutsaers et al., "Structural studies of the carbohydrate chains of human γ-interferon", *Eur. J. Biochem.* 156:651-654 (1986).

Napier, "Isoelectric Focusing of Human Urinary Erythropoietin", *IRCS Med. Sci. Biochem.* 4:437 (1976).

Narhi et al. (1991), "The Effect of Carbohydrate on the Structure and Stability of Erythropoietin," *J. Biol. Chem.* 266:23022-23026.

Papayannopoulou et al., "Globin Phenotypes and Surface Markers of Two New Human Erythroleukemia Lines", *Blood* 64(supp. 1):116a (1984).

Phelps et al., "An Electrophoretic and Immunochemical Characterization of Human Surfactant-Associated Proteins", *Biochem. Biophys. Acta.* 791:226-238 (1984).

Pierce et al., "Glycoprotein Hormones: Structure and Function", *Ann. Rev. Biochem.* 50:465-495 (1981).

Quelle et al. (1989), "High-Level Expression and Purification of a Recombinant Human Erythropoietin Produced Using a Baculovirus Vector," *Blood* 74(2):652-657.

Radola (1973), "IsoElectric Focusing in Layers of Granulated Gels in Preparative Isoelectric Focusing," *Biochim. et Biophysic.* 295:412-428.

Radola (1974), "IsoElectric Focusing in Layers of Granulated Gels in Preparative Isoelectric Focusing," *Biochim. et Biophysic.* 386:181-195.

Recny et al. (1987), "Structural Characterization of Natural Human Urinary and Recombinant DNA-derived Erythropoietin," *J. Biol. Chem.* 262(35):17156-17163.

Sasaki et al. (1987), "Carbohydrate Structure of Erythropoietin Expressed in Chinese Hamster Ovary Cells by a Human Erythropoietin cDNA," *J. Biol. Chem.* 262(25):12059-12076.

Sasaki et al. (1988), "Site-Specific Glycosylation of Human Recombinant Erythropoietin Analysis of Glycopeptides or Peptides at Each Glycosylation Site by Fast Atom Bombardment Mass Spectrometry," *Biochemistry.* 22:8168-8626.

Schneider et al. "Homodimerization of Erythropoietin Receptor by a Bivalent Monoclonal Antibody Triggers Cell Proliferation and Differentiation of Erythroid Precursors," *Blood* 89(2):473-482.

Shelton et al., "Physicochemical Properties of Erythropoietin: Isoelectric Focusing and Molecular Weight Studies", *Biochem. Med* 12:45-54 (1975).

Syed et al. (1998), "Efficiency of signaling through cytokine receptors depends critically on receptor orientation," *Nature* 395:511-516.

Takeuchi et al., "Comparative Study of the Asparagine-linked Sugar Chains of Human Erythropoietins Purified from Urine and the Culture Medium of Recombinant Chinese Hamster Ovary Cells", *J. Biol. Chem.* 263:3657-3663 (1988).

Takeuchi et al., "Sensitive Method for Carbohydrate Composition Analysis of Glycoproteins by High-Performance Liquid Chromatography", *J. Chromatogr.* 400:207-213 (1987).

Takeuchi et al. (1989), "Relationship between sugar chain structure and biological activity of Recombinant Human Erythropoietin Produced in Chinese Hamster Ovary Cells," *PNAS* 86:7819-7822.

Takeuchi et al. (1990), "Role of Sugar Chains in the in Vitro Biological Activity of Human Erythropoietin Produced in Recombinant Chinese Hamster Ovary Cells," *J. Biol. Chem.* 265:12127-12130.

Tsuda et al. (1990), "The role of carbohydrate in recombinant human erythropoietin," *Eur. J. Biochem.* 188:405-411.

Tsuda et al. (1988), "Comparative Structural Study of N-Linked Oligosaccharides of Urinary and Recombinant Erythropoietins," *Biochemistry* 27:5646-5654.

Vanrenterghem et al., *J. Am. Soc. Nephrol.* 10:270A (1999), Abstract A1365.

Varki (1993), "Biological roles of oligosaccharides: all of the theories are correct," *Glycobiology* 3:97-130.

Wasley et al. (1991), "The Importance of N- and O-Linked Oligosaccharides for the Biosynthesis and In Vitro and In Vivo Biologic Activities of Erythropoietin," *Blood* 77:2624-2632.

Webber et al. (1983), "Purification of Erythropoietin from Human Urine," *Fedn. Proc.* 42(S672):1872.

Yamaguchi et al., "Effects of Site-directed Removal of N-Glycosylation Sites in Human Erythropoietin on its Production and Biological Properties", *J. Biol. Chem.* 266:20434-20439 (1991).

Yanisch-Perron et al., "Improved M13 phage cloning vectors and host strains: nucleotide sequences of the M13mp18 and pUC19 vectors", *Gene* 33:103-119 (1985).

T.W. Strickland, Abstract and Poster at the Keystone Symposium on Glycobiology, Mar. 1992, Abstract P324.

* cited by examiner

FIG. 5

```
-27                                      +1        10          20    □
  MGVHECPAWLWLLLSLLSLPLGLPVLGAPPRLICDSRVLERYLLEAKEAENIT
                                     ↓↓      ↓↓
                                     NS      NS
                                     □       □

30       □40        50          60         70
  TGCAEHCSLNENITVPDTKVNFYAWKRMEVGQQAVEVWQGLALLSEAVLRGQA
                                              ↓
                                              N
                                              □

*
                                                      T
                                                      ↑
  80   □     90        100        110       120    ↑ * 130
  LLVNSSQPWEPLQLHVDKAVSGLRSLTTLLRALGAQKEAISPPDAASAAPLRT
                                              ↓↓ ↓
                                              NN  S
                                              □□
```

```
     140       150       160                    □ = Site for N-glycosylation
  ITADTFRKLFRVYSNFLRGKLKLYTGEACRTGDR
                       ↓↓                       * = Site for O-glycosylation
                       NS
                       □
```

GLYCOSYLATION ANALOGS OF ERYTHROPOIETIN

This is a continuation of U.S. Ser. No. 08/108,016, filed Aug. 17, 1993, now abandoned, which is a continuation in part of U.S. Ser. No. 07/942,126, filed Sep. 8, 1992, now abandoned, which is a continuation of U.S. Ser. No. 07/594,448, filed Oct. 12, 1990, which is a continuation in part of U.S. Ser. No. 07/421,444, filed Oct. 13, 1989, now abandoned. The present invention relates to erythropoietin analogs having at least one additional site for glycosylation or a rearrangement of at least one site for glycosylation. The invention also relates to DNA sequences encoding said erythropoietin analogs, and recombinant plasmids and host cells for analog expression.

BACKGROUND OF THE INVENTION

Erythropoietin (EPO) is a glycoprotein hormone involved in the maturation of erythroid progenitor cells into erythrocytes. It is essential in regulating levels of red blood cells in circulation. Naturally occurring erythropoietin is produced by the liver during fetal life and by the kidney of adults and circulates in the blood and stimulates the production of red blood cells in bone marrow. Anemia is almost invariably a consequence of renal failure due to decreased production of erythropoietin from the kidney. Recombinant erythropoietin produced by genetic engineering techniques involving the expression of a protein product from a host cell transformed with the gene encoding erythropoietin has been found to be effective when used in the treatment of anemia resulting from chronic renal failure.

Low levels of erythropoietin are normally present in human urine, while individuals suffering from aplastic anemia exhibit elevated levels of urinary erythropoietin. The purification of human urinary erythropoietin by Miyake et al. in J. Biol. Chem., 252, 5558 (1977), used, as starting material, urine from aplastic anemic individuals. To date, however, urinary erythropoietin has not been shown to be therapeutically useful.

The identification, cloning, and expression of genes encoding erythropoietin are described in U.S. Pat. No. 4,703,008 to Lin, the disclosure of which is incorporated herein by reference. A description of a method for purification of recombinant erythropoietin from cell medium is included in U.S. Pat. No. 4,667,016 to Lai et al. The expression and recovery of biologically active recombinant erythropoietin from mammalian cell hosts containing the erythropoietin gene on recombinant plasmids has, for the first time, made available quantities of erythropoietin suitable for therapeutic applications. In addition, knowledge of the gene sequence and the availability of larger quantities of purified protein has led to a better understanding of the mode of action of this protein.

Many cell surface and secretory proteins produced by eucaryotic cells are modified with one or more oligosaccharide groups. This modification, referred to as glycosylation, can dramatically affect the physical properties of proteins and can also be important in protein stability, secretion, and subcellular localization. Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

Glycosylation occurs at specific locations along the polypeptide backbone and is usually of two types: O-linked oligosaccharides are attached to serine or threonine residues while N-linked oligosaccharides are attached to asparagine residues when they are part of the sequence Asn-X-Ser/Thr, where X can be any amino acid except proline. The structures of N-linked and O-linked oligosaccharides and the sugar residues found in each type are different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein.

Both human urinary derived erythropoietin and recombinant erythropoietin (expressed in mammalian cells) having the amino acid sequence 1–165 of human erythropoietin contain three N-linked and one O-linked oligosaccharide chains which together comprise about 40% of the total molecular weight of the glycoprotein. N-linked glycosylation occurs at asparagine residues located at positions 24, 38 and 83 while O-linked glycosylation occurs at a serine residue located at position 126 (Lai et al. J. Biol. Chem. 261, 3116 (1986); Broudy et al. Arch. Biochem. Biophys. 265, 329 (1988)). The oligosaccharide chains have been shown to be modified with terminal sialic acid residues. Enzymatic treatment of glycosylated erythropoietin to remove all sialic acid residues results in a loss of in vivo activity but does not affect in vitro activity (Lowy et al. Nature 185, 102 (1960); Goldwasser et al. J. Biol. Chem. 249, 4202 (1974)). This behavior has been explained by rapid clearance of asialoerythropoietin from circulation upon interaction with the hepatic asialoglycoprotein binding protein (Morrell et al. J. Biol. Chem. 243, 155 (1968); Briggs, et al. Am. J. Physiol. 227, 1385 (1974); Ashwell et al. Methods Enzymol. 50, 287 (1978)). Thus, erythropoietin possesses in vivo biological activity only when it is sialylated to avoid its binding by the hepatic binding protein.

The role of the other components in the oligosaccharide chains of erythropoietin is not well defined. It has been shown that partially deglycosylated erythropoietin has greatly reduced in vivo activity compared to the glycosylated form but does retain in vitro activity (Dordal et al. Endocrinology 116, 2293 (1985); Lin patent, supra). In another study, however, the removal of N-linked or O-linked oligosaccharide chains singly or together by mutagenesis of asparagine or serine residues that are glycosylation sites sharply reduces in vitro activity of the altered erythropoietin that is produced in mammalian cells (Dube et al. J. Biol. Chem. 263, 17516 (1988)).

Glycoproteins such as erythropoietin can be separated into different charged forms using techniques such as isoelectric focusing (IEF). Several parties have reported IEF studies of crude and partially purified erythropoietin preparations (Lukowsky et al., J. Biochem 50, 909 (1972); Shelton et al. Biochem. Med. 12, 45 (1975); Fuhr et al. Biochem. Biophys. Res. Comm. 98, 930 (1981)). At most, three or four fractions having erythropoietin activity were distinguished by IEF in these studies and none were characterized with respect to carbohydrate content. In addition, no correlation between the isoelectric points of the fractions and their biological activity was made.

During the purification of urinary erythropoietin from human urine discussed in Miyake et. al. supra, two erythropoietin fractions from hydroxylapatite chromatography designated II and IIIA were reported to have similar specific activity. A subsequent carbohydrate analysis of fractions II and IIIA revealed that fraction II had a greater average sialic acid content than fraction IIIA (Dordal et. al. supra).

It is an object of the present invention to provide separated and isolated isoforms of erythropoietin having a defined sialic acid content and biological activity. Pharmaceutical compositions containing such molecules would have therapeutic benefit.

SUMMARY OF THE INVENTION

The subject invention relates to analogs of human erythropoietin comprising an amino acid sequence which includes at least one additional site for glycosylation. The added sites for glycosylation may result in a greater number of carbohydrate chains, and higher sialic acid content, than human erythropoietin. Erythropoietin analogs comprising amino acid sequences which include the rearrangement of at least one site for glycosylation are also provided. Analogs comprising an addition of one or more amino acids to the carboxy terminal end of erythropoietin wherein the addition provides at least one glycosylation site are also included. The invention further encompasses DNA sequences encoding such erythropoietin analogs, and recombinant plasmids and host cells for analog expression.

BRIEF DESCRIPTION OF THE DRAWINGS

FIG. 5 shows the amino acid sequence of human erythropoietin (SEQ ID NO:26). Squares indicate asparagine residues to which N-linked carbohydrate chains are attached and an asterisk indicates the serine residue modified with an O-linked carbohydrate chain.

DETAILED DESCRIPTION OF THE INVENTION

Figure 1:
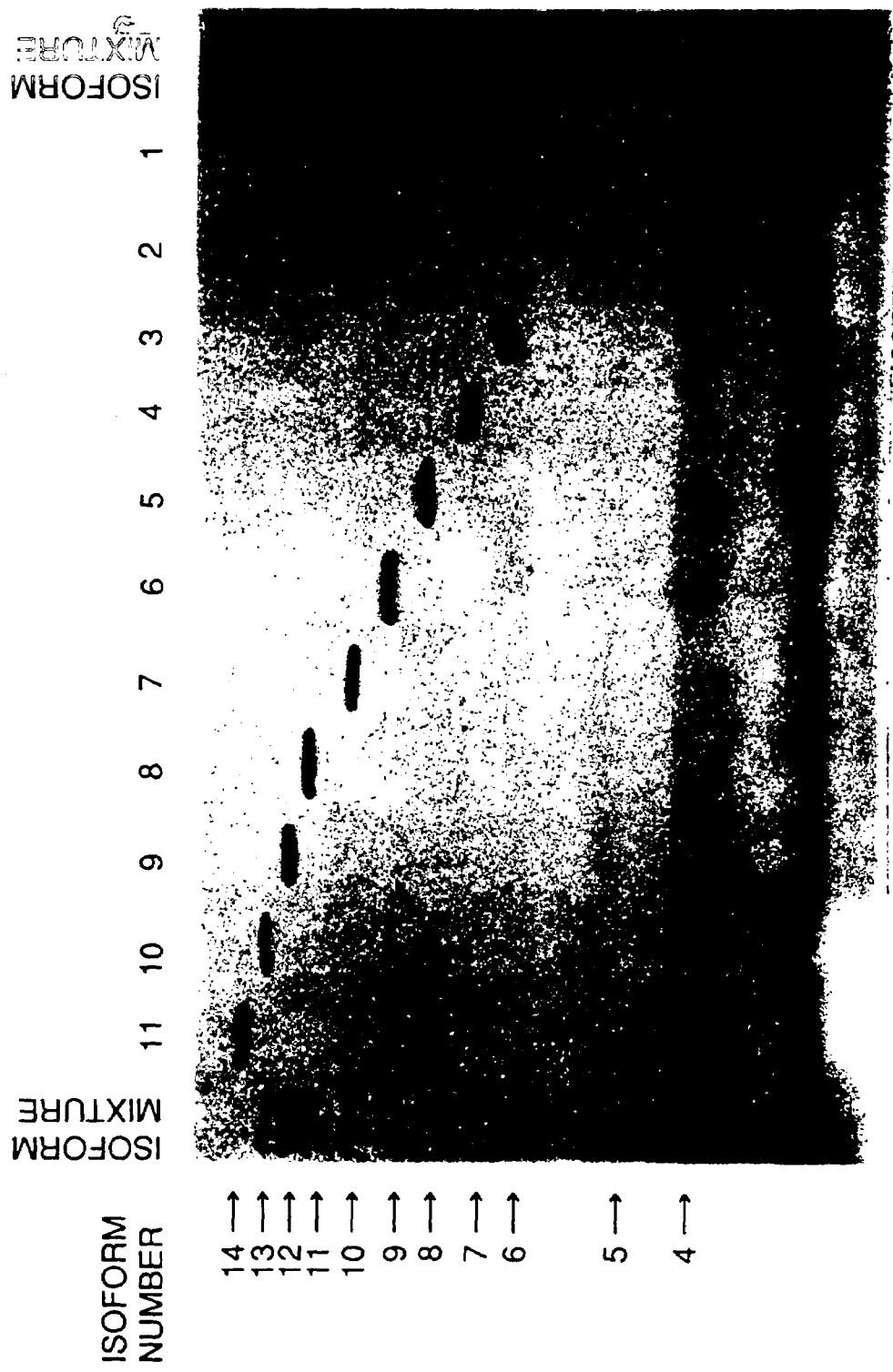
FIG. 1 shows an analytical isoelectric focusing gel of the separate recombinant erythropoietin isoforms. Gel lanes 1–11 show isoforms ranging from less acidic (higher pI) in lane 1 to more acidic (lower pI), in lane 11. Purified recombinant erythropoietin containing a mixture of isoforms 9–14 is also shown in the far left and right lanes of the gel.

The subject invention provides erythropoietin isoforms. The specific isoforms of erythropoietin obtained in accordance with the present invention, and their properties, may vary depending upon the source of the starting material. For example, the isoforms of urinary derived human erythropoietin are different than the isoforms of recombinant erythropoietin. In a preferred embodiment, the invention relates to an erythropoietin isoform having a specific number (i.e. a fixed number greater than 0) of sialic acids per erythropoietin molecule, said number selected from the group consisting of 1–14. Advantageously said number is 9, 10, 11, 12, 13, or 14. In another embodiment, said number is greater than 14, advantageously 16–23.

The term "erythropoietin isoform" as used herein refers to erythropoietin preparations having a single isoelectric point (pI), and having the same amino acid sequence. The term "erythropoietin", as used herein, includes naturally occurring erythropoietin, urinary derived human erythropoietin as well as non-naturally occurring polypeptides having an amino acid sequence and glycosylation sufficiently duplicative of that of naturally occurring erythropoietin to allow possession of in vivo biological properties of causing bone marrow cells to increase production of reticulocytes and red blood cells.

It has been found that discrete isoforms of recombinant erythropoietin having the amino acid sequence of urinary derived human erythropoietin correspond to erythropoietin molecules having from 1–14 sialic acids, and each isoform present in purified recombinant erythropoietin has an in vivo activity which is related to the number of sialic acids the isoform possesses.

In a preferred embodiment, erythropoietin is the product of the expression of an exogenous DNA sequence that has been transfected into a non-human eucaryotic host cell, that is, in a preferred embodiment the erythropoietin is "recombinant erythropoietin". Recombinant erythropoietin is advantageously produced according to the procedures described in commonly owned Lin U.S. Pat. No. 4,703,008 hereby incorporated by reference. Recombinant erythropoietin can be purified according to the general procedures described in Example 2 of commonly owned Lai et al. U.S. Pat. No. 4,667,016 hereby incorporated by reference, or alternatively according to the procedure described in Example 2 of Lai et al. wherein DEAE-Agarose chromatography is replaced by Q-Sepharose chromatography.

Erythropoietin purified according to Example 2 of Lai et al. supra contains predominantly six isoforms when analyzed by IEF. In addition, at least one additional isoform of greater acidity has been detected using the chromatographic procedures described in Example 4. (This more acidic form, migrating at >14 sialic acids on an IEF gel may contain nonsialic acid negative charges as shown by the resistance of some of the charge to sialidase digestion). These isoforms differ from each other by sialic acid content. As shown in the Examples, this is demonstrated by isolating 10 of these isoforms by preparative IEF and determining the sialic acid content of five of them. Of the isoforms assayed for sialic acid content, it is found that the five isoforms contained either 9, 10, 11, 12 or 13 sialic acid residues.

There is a relationship between the relative in vivo specific activity of erythropoietin and number of sialic acid residues per erythropoietin molecule from the isoforms 5 through 11 (each isoform is designated herein by the number of sialic acids per erythropoietin molecule). Isoforms 11 through 14 have approximately the same relative in vivo specific activity. Isoforms 5–14 were assayed for in vivo activity by the exhypoxic polycythemic mouse bioassay and the amount of each isoform present is determined by Bradford protein assay, absorbance at 280 nm or by radioimmunoassay (RIA) for erythropoietin. RIA determinations (Egrie et al. Immunobiology 172, 213, (1986)), expressed as units/ml, are divided by 212, 770 units/mg erythropoietin polypeptide, the average specific activity of purified erythropoietin as determined by RIA, to give protein concentrations of isolated isoforms or isoform mixtures expressed as mg erythropoietin polypeptide/ml. As shown in the Examples, the relative in vivo specific activities increase step-wise from isoform 5 to isoform 11 (see Table 2).

The in vivo specific activities referred to herein are measurements of relative in vivo specific activities and are not measurements of absolute in vivo specific activities. For the purposes of this application, the specific activities are used only to compare relative activities of isoforms that have been assayed using the same assay, using the same conditions including the same internal standard, the same type of animals, having the same analysis of the data used to calculate specific activity, the same assay for determining protein content. It is not intended that any in vivo specific activity value reported for any isoform represents an inherent or absolute value for that isoform.

This invention also provides compositions comprising two or more erythropoietin isoforms. In one embodiment the compositions comprise a mixture of isoforms having greater than a predetermined number of sialic acids per erythropoietin molecule, e.g. greater than 11 sialic acids per erythropoietin molecule, or greater than 12 sialic acids per molecule, e.g. a mixture of isoforms 12, 13 and 14. In another embodiment the compositions comprise mixtures of isoforms having a predetermined number of sialic acids per erythropoietin molecule, e.g. less than 12, but greater than 8 sialic acids per molecule as in, for example, a mixture of isoforms 9, 10, and 11. The invention also provides for compositions of erythropoietin isoforms wherein the relative amounts of the isoforms are the same or different. For example, a mixture of isoforms 9, 10 and 11 could have the isoforms present in a variety of ratios such as 1:1:1, 2:3:1 or 20:20:1.

Advantageously, the compositions comprise mixtures of less than four isoforms, for example a mixture of isoforms 11, 12, and 13, or a mixture of 12 and 14, or a mixture of 7 and 13.

In order to produce mixtures of erythropoietin isoforms, this invention also provides methods of isolating selected erythropoietin isoforms simultaneously. These methods include isolation of individual isoforms by techniques such as preparative isoelectric focusing or preparation of mixtures of isoforms having a predetermined number of sialic acids per molecule (for example, greater than 11) by techniques such as ion exchange chromatography or chromatofocusing. All of these techniques have as their basis the separation of proteins according to charge.

In general, ion exchange chromatography and chromatofocusing involve application of either crude human erythropoietin (cell conditioned media) or purified material to a column resin under conditions that permit binding of some or all of the erythropoietin isoforms to the resin. For crude erythropoietin preparations, it is preferable to apply the protein to the column at about pH 7 while for purified preparations the protein can be applied to the column at pH 7 down to about pH 4. After washing the column with buffer at about pH 4, those erythropoietin isoforms that remain bound on the ion exchange column are eluted by increasing the pH and the salt concentration of the buffer or by applying a gradient of decreasing pH and increasing ionic strength at about pH 4. For chromatofocusing, the isoforms are eluted from the column by a gradient of decreasing pH or by washing the column with a high concentration of salt.

In a preferred embodiment, individual isoforms are isolated using ion exchange chromatography. As an example, isoform 14 was isolated using ion exchange chromatography as described in Example 8.

Also encompassed by the invention are certain analogs of human erythropoietin. As used herein the phrase "analog of human erythropoietin" refers to erythropoietin with one or more changes in the amino acid sequence of human erythropoietin which result in an increase in the number of sites for sialic acid attachment. Analogs are generated by site-directed mutagenesis having additions, deletions, or substitutions of amino acid residues that increase or alter sites that are available for glycosylation. Such analogs may have a greater number of carbohydrate chains than human erythropoietin.

The erythropoietin analogs of the present invention comprise an amino acid sequence which includes at least one additional site for glycosylation. Analogs having levels of sialic acid greater than those found in human erythropoietin are generated by adding glycosylation sites which do not perturb the secondary or tertiary conformation required for biological activity. Advantageously, the analog of human erythropoietin has 1, 2 or 3 additional sites for N-glycosylation or O-glycosylation, resulting in the addition of 1, 2, or 3 additional N-linked or O-linked carbohydrate chains. For example, a leucine at position 69 is replaced by an asparagine to give the sequence Asn-Leu-Ser, which serves as a fourth site for N-glycosylation. Such a change can commonly provide up to four additional sialic acids per molecule. Examples of changes that generate additional O-glycosylation sites are alanine at position 125 to threonine and alanines at positions 124 and 125 to proline and threonine, respectively. Analogs may be constructed which have one or more additional N-linked and O-linked chains, for example, analogs NO1 and NO2 described in Table 5. As will be appreciated by those skilled in the art, the subject invention includes many other analogs of human erythropoietin having additional sites for glycosylation.

Analogs having increased levels of carbohydrate attachment at a glycosylation site are also encompassed by the invention. Such analogs usually involve the substitution of one or more amino acids which are in close proximity to an N-linked or O-linked site. As a result of these amino acid changes, a greater proportion of erythropoietin polypeptides will have a carbohydrate modification. The glycosylation sites may be naturally occurring or generated by mutation. For example, analog N13 does not generate an additional carbohydrate chain even though a glycosylation site was introduced at position 88. However, analogs N14 ad 18, which have serine and valine residues, respectively, substituted at position 87, have an additional carbohydrate chain at position 88.

Also provided by the invention are analogs which have one or more amino acids extending from the carboxy terminal end of erythropoietin and wherein the carboxy terminal extension provides at least one additional carbohydrate site. In one embodiment, an analog was constructed by fusing the carboxy-terminal 28 amino acids of human chorionic gonadotropin (HCG) to the arginine residue at position 166 of human erythropoietin. The HCG carboxy-terminal fragment has four sites for O-glycosylation (Kessler et al., J. Biol. Chem. 254, 7907 (1979)).

Tables 3, 4 and 5 list erythropoietin analogs which have additional sites for N-linked and/or O-linked carbohydrate chains. The analogs have the sequence Asn-X-Ser/Thr substituted at various positions in the human erythropoietin polypeptide chain to create N-linked sites or have serine or threonine residues introduced to create O-linked sites.

Table 6 lists those analogs which add at least one additional N-linked or one additional O-linked carbohydrate chain, or add additional N-linked and O-linked chains simultaneously, as evidenced by the migration of the glycoproteins on SDS gels (Example 7). As can be appreciated from Tables 3–6, analogs having one or more additional sites for carbohydrate attachment do not necessarily result in erythropoietin molecules having additional carbohydrate chains. For example, substitution of threonine residues at positions 123 and 125 resulted in the addition of an O-linked carbohydrate chain while substitution of serine or threonine at other positions did not result in analogs with additional O-linked chains (see Table 4). However, substitution of asparagine residues at positions 30, 51, 57, 69, 88, 89, 136 and 138 in the human erythropoietin amino acid sequence resulted in the addition of an N-linked chain at those sites. The fusion of an HCG polypeptide fragment to the arginine residue at position 166 of human erythropoietin resulted in an erythropoietin-HCG fusion molecule having at least two additional O-linked carbohydrate chains.

The erythropoietin analogs of the present invention also encompass erythropoietin having an amino acid sequence which includes a rearrangement of at least one site for glycosylation. A rearrangement of a glycosylation site as used herein refers to the deletion of one or more glycosylation sites in human erythropoietin and addition of one or more non-naturally occurring glycosylation sites. Analogs R1, R2 and R3 are examples of such rearrangements and were constructed by deletion of the N-linked sites at positions 24, 38 or 83, respectively, and addition of an N-linked site at position 88. However, numerous other types of carbohydrate site rearrangements are possible and the resulting analogs may or may not have a greater number of glycosylation sites compared to human erythropoietin.

Analogs R1, R2 and R3 were analyzed for in vivo biological activity and the results shown in Table 7. The introduction of an N-linked chain at Asn 88 restored biological activity to erythropoietin having any one of the three naturally occurring N-linked sites deleted. These results indicate that the positions of carbohydrate chains in erythropoietin may be changed in order to generate useful analogs without significantly affecting the biological activity.

Also encompassed by the present invention are DNA sequences encoding erythropoietin analogs having additional sites for N-linked and/or O-linked chains, analogs having a rearrangement of at least one attachment site for a carbohydrate chain, and analogs having one or more amino acids extending from the carboxy-terminal end of erythropoietin. Procedures used to introduce changes into the human erythropoietin DNA sequence for the purpose of creating and altering attachment sites for carbohydrates are disclosed in Example 6.

These erythropoietin analogs can be the product of expression of an exogenous DNA sequence, i.e., produced through recombinant DNA technology, or can be synthesized products. An exogenous DNA sequence comprises cDNA, genomic DNA or chemically synthesized DNA encoding an erythropoietin analog. Recombinant DNA plasmids and eucaryotic host cells useful for the expression of said analogs are also provided. Expression vectors include any vector which is capable of expressing cloned DNA sequences in a eucaryotic host cell, particularly those vectors used for expression in COS and CHO cells. Examples of such vectors include plasmids pEC and pDECΔ described in Example 6 of the specification. The cultivation of COS and CHO host cells expressing erythropoietin analogs was carried out using procedures known to one skilled in the art.

Isolated isoforms and mixtures of isoforms derived from erythropoietin analogs are obtained using the methods described above for preparing isoforms of human erythropoietin. These methods may include isoelectric focusing, ion exchange chromatography and chromatofocusing. Preferably, ion exchange chromatography is used to prepare individual isoforms and mixtures of isoforms derived from erythropoietin analogs.

Increasing the number of carbohydrate chains on erythropoietin, and therefore the number of sialic acids per erythropoietin molecule, may confer advantageous properties such as increased solubility, greater resistance to proteolysis, reduced immunogenicity, increased serum half-life, and increased biological activity.

Conditioned media from CHO cells expressing erythropoietin analogs were analyzed for in vivo biological activity and the results shown in Table 6. Several analogs tested had activity that was 3-fold or more higher than human erythropoietin. In particular, analogs having an additional N-linked carbohydrate chain at either position 30 or 88 show 2- to 3-fold higher activity than human erythropoietin while analogs having additional O-linked chains as a result of fusion of human erythropoietin to the HCG polypeptide fragment have at least 2-fold higher activity.

Two erythropoietin analogs having additional carbohydrate chains were purified and isoform mixtures having different sialic acid contents were isolated (Example 8). $Thr^{125}$ and $Ser^{87}Asn^{88}Thr^{90}$ (EPO N14) analogs were separated into three separate isoform fractions and the in vivo biological activities for each fractions was determined. The results presented in Table 8 demonstrate that EPO N14 isoform fractions having higher sialic acid content have a greater in vivo activity.

Figure 13:
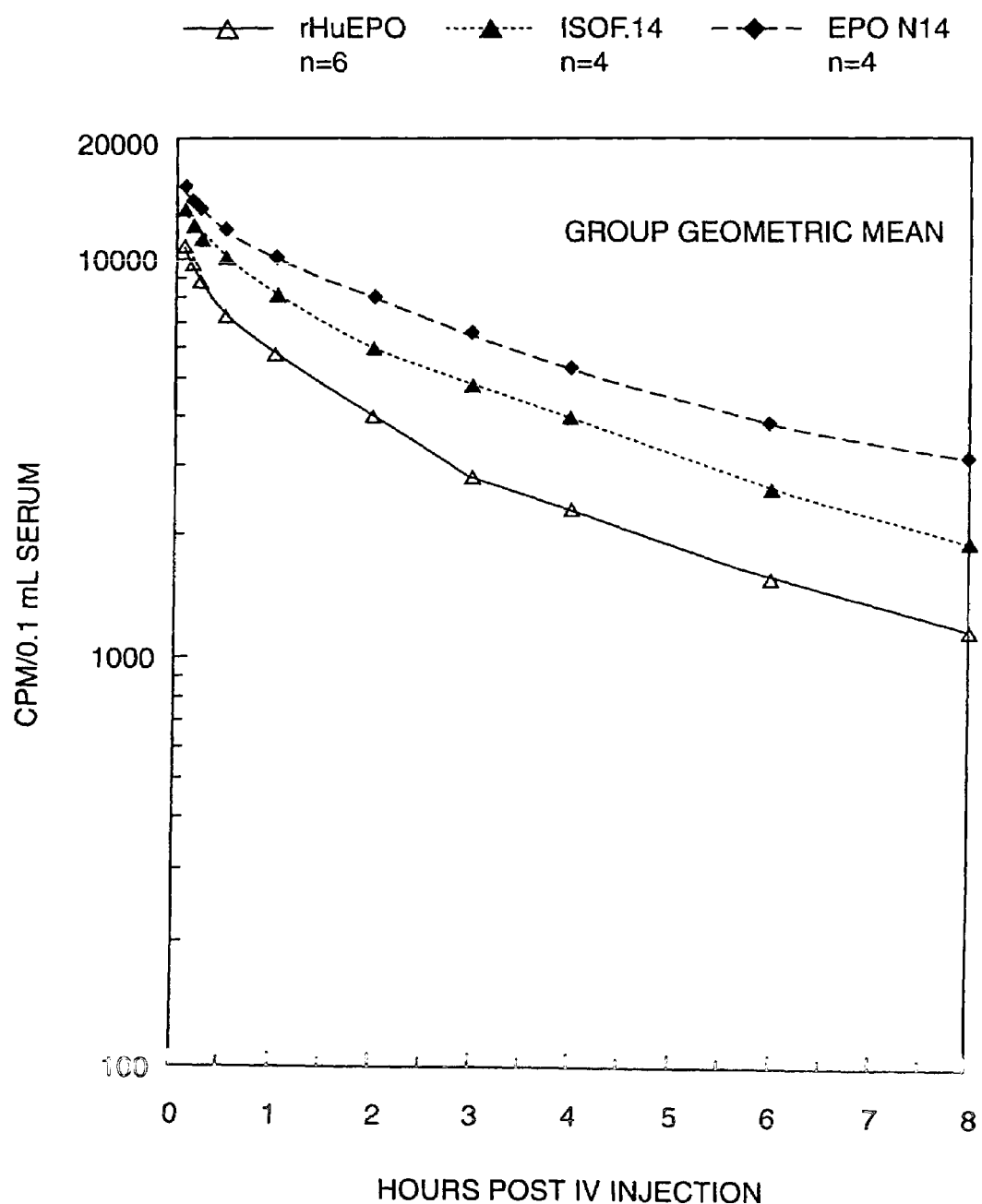
FIG. 13 shows the pharmacokinetics of recombinant human erythropoietin, isolated isoform 14 and EPO N14 analog (isoforms 15–17) after intravenous injection into rats.
Figure 14:
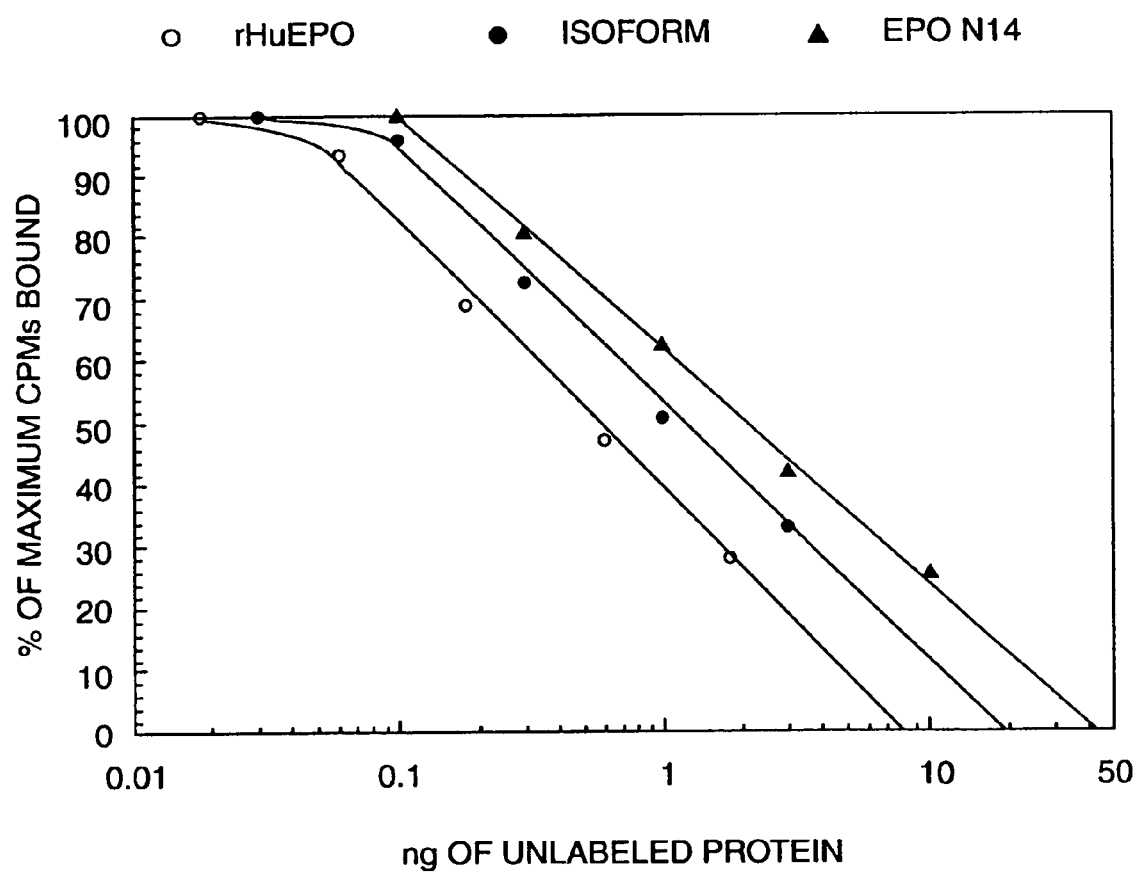
FIG. 14 shows a cold displacement assay of $^{125}$I labeled recombinant human erythropoietin binding to the erythropoietin receptor in the presence of varying amounts of unlabeled rHuEPO, isolated isoform 14 or EPO N14 analog.
Figure 15:
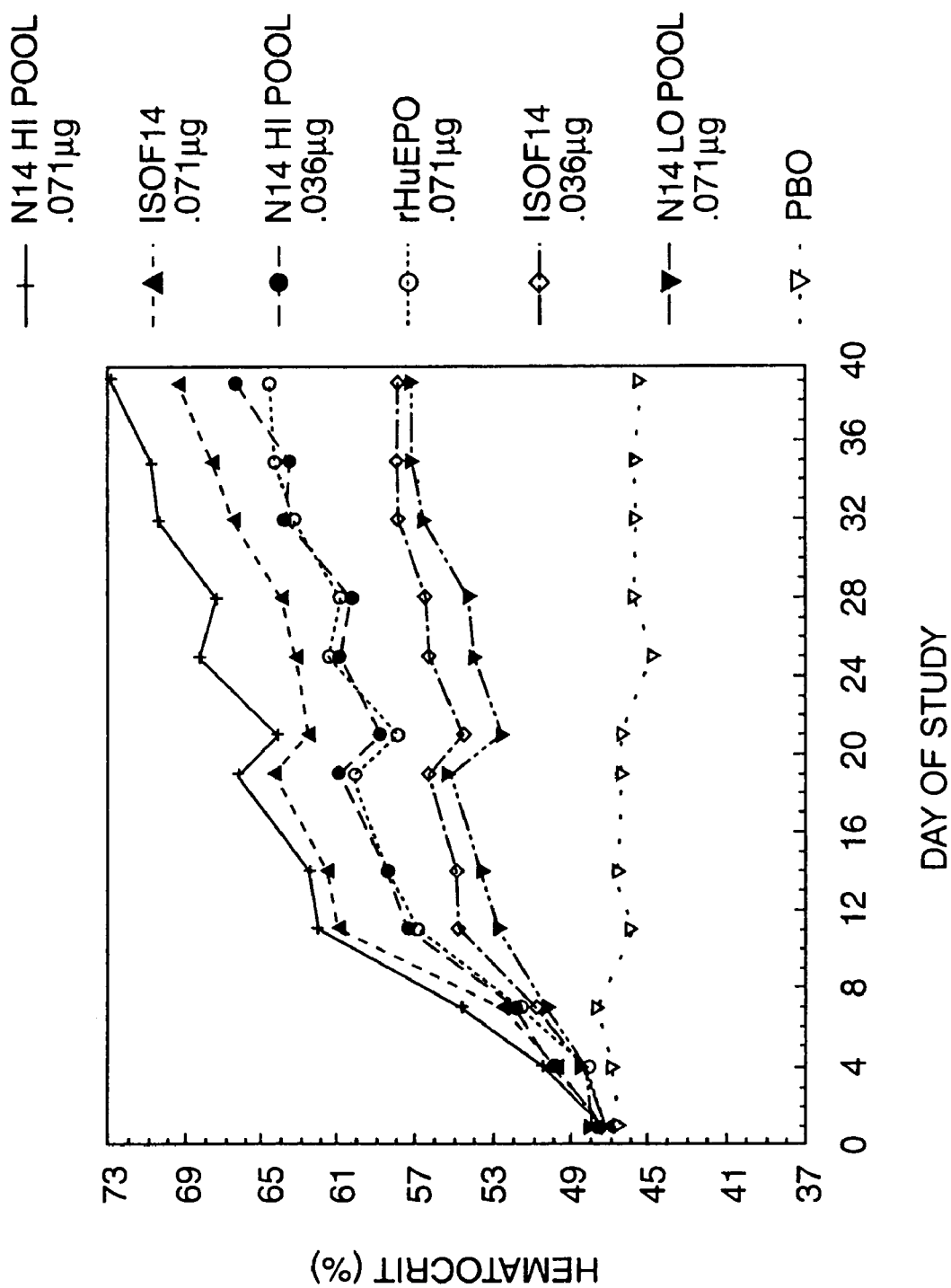
FIG. 15 shows a mouse hematocrit study comparing the activity of EPO N14 high isoform pool (0.036 and 0.0712 μg), isolated isoform 14 (0.036 and 0.0712 μg), EPO 177 low isoform pool (0.0712 μg) and rHuEPO (0.071 μg).

A pool of high sialic acid isoforms of EPO N14 analog and recombinant human erythropoietin (isoforms 9–14) were studied in receptor binding assays, pharmacokinetic experiments, and experiments to determine increase in hematocrit of mice. Results of these assays indicate that there is a direct relationship between sialic acid content, clearance half-life, and ability to increase the hematocrit of treated mice. Thus, as shown in FIGS. 13, 14 and 15, EPO N14 high sialic acid isoform pool had a significantly longer in vivo half-life and promoted a greater increase in hematocrit than did either isolated isoform 14 or recombinant human erythropoietin, even though the N14 high sialic acid isoform pool did not bind as strongly to the receptor.

Another embodiment of the invention relates to mammalian (e.g., Chinese Hamster Ovary, CHO) host cells which preferentially synthesize isoforms of human erythropoietin or erythropoietin analogs having greater than a specific number of sialic acids per molecule, e.g. greater than 10 sialic acids per molecule. Erythropoietin molecules have N-linked and O-linked oligosaccharides structures which can limit the sialic acid content of the molecule. For example, tetraantennary (four-branched) N-linked oligosaccharides most commonly provide four possible sites for sialic acid attachment while bi- and triantennary oligosaccharide chains, which can substitute for the tetraantennary form at asparagine-linked sites, commonly have at most only two or three sialic acids attached. O-linked oligosaccharides commonly provide two sites for sialic acid attachment. Thus, erythropoietin molecules can accommodate a total of 14 sialic acid residues provided all three N-linked oligosaccharides are tetraantennary. Mammalian cell cultures are screened for those cells that preferentially add tetraantennary chains to recombinant erythropoietin, thereby maximizing the number of sites for sialic acid attachment.

The N-linked oligosaccharides of urinary erythropoietin contain sialic acid in both an α 2,3 and an α 2,6 linkage to galactose (Takeuchi et al. J. Biol. Chem. 263, 3657(1988)). Typically the sialic acid in the α 2,3 linkage is added to galactose on the mannose α 1,6 branch and the sialic acid in the α 2,6 linkage is added to the galactose on the mannose α 1,3 branch. The enzymes that add these sialic acids (β-galactoside α 2,3 sialyltransferase and β-galactoside α 2,6 sialyltransferase) are most efficient at adding sialic acid to the mannose α 1,6 and mannose α 1,3 branches respectively.

Dihydrofolate reductase (DHFR) deficient Chinese Hamster Ovary (CHO) cells are a commonly used host cell for the production of recombinant glycoproteins including recombinant erythropoietin. These cells do not express the enzyme β-galactoside α 2,6 sialyltransferase and therefore do not add sialic acid in the α 2,6 linkage to N-linked oligosaccharides of glycoproteins produced in these cells. (Mutsaers et al. Eur. J. Biochem. 156, 651 (1986); Takeuchi et al. J. Chromatogr. 400, 207 (1987)). Consequently, recombinant erythropoietin produced in CHO cells lacks sialic acid in the 2,6 linkage to galactose (Sasaki et al. (1987), supra; Takeuchi et al. (1987), supra).

In another embodiment of the subject invention, human erythropoietin or an erythropoietin analog is produced in CHO cells that are transfected with a functional β-galactoside α 2,6 sialyltransferase gene to give incorporation of sialic acid in α 2,6 linkage to galactose. The resulting isoforms will contain sialic acid having both α 2,3 and α 2,6 linkages to galactose. See Lee et al. J. Biol. Chem. 264, 13848 (1989), hereby incorporated by reference, for a disclosure of techniques for creating modified CHO cells or other mammalian host cells.

Also comprehended by the invention are pharmaceutical compositions comprising a therapeutically effective amount of a specific isoform or mixture of isoforms together with a suitable diluent, adjuvant and/or carrier useful in erythropoietin therapy. Pharmaceutical compositions comprising a therapeutically effective amount of an erythropoietin analog together with a suitable diluent, adjuvant and/or carrier are also encompassed. A "therapeutically effective amount" as used herein refers to that amount which provides therapeutic effect for a given condition and administration regimen. The administration of isoforms of human erythropoietin or erythropoietin analogs is preferably by parenteral routes. The specific route chosen will depend upon the condition being treated. The administration of isoforms of human erythropoietin or erythropoietin analogs is preferably done as part of a formulation containing a suitable carrier, such as human serum albumin, a suitable diluent, such as a buffered saline solution, and/or a suitable adjuvant. The required dosage will be in amounts sufficient to raise the hematocrit of patients and will vary depending upon the severity of the condition being treated, the method of administration used and the like.

The following examples are offered to more fully illustrate the invention, but are not to be construed as limiting the scope thereof. The erythropoietin standard used in the in vivo bioassays employed in the Examples is a recombinant erythropoietin standard that was standardized against a partially purified urinary erythropoietin standard. Thus, only relative in vivo specific activities are being measured. Also the in vivo specific activities are expressed in "units/ml", "units/mg" and units/$A_{280}$" and not as "IU/ml", "IU/mg" and IU/$A_{280}$" because the erythropoietin standard employed has not been directly correlated to any existing international standard.

EXAMPLE 1

Isolation of Recombinant Erythropoietin Isoforms

Recombinant erythropoietin is produced as described in Lin, supra. Recombinant erythropoietin used as starting material for the first and third isoform isolations is purified according to the procedure described in Example 2 of commonly owned Lai et al., supra. Starting material for the second and fifth isoform isolation is purified according to Lai et al. supra using the modification of Q-Sepharose chromatography. These preparations contain a mixture of isoforms of recombinant erythropoietin having the same amino acid sequence as urinary derived human erythropoietin and contain predominantly isoforms 9 to 14. Starting material for the fourth isoform preparation is the material which elutes during the 5 mM acetic acid/1 mM glycine/6M urea wash of the anion exchange column in Example 2 of Lai et al. This fraction contains isoforms with less than or equal to 9 sialic acids and was further purified by gel filtration chromatography as described in Example 2 of Lai et al. prior to use in the preparative isoelectric focusing procedure. The sixth isoform preparation used as its starting material a purified preparation of recombinant erythropoietin having from 4 to 13 sialic residues. This material was purified as per Example 2 of Lai et al. except for a modification to the ion exchange column (elution of the recombinant erythropoietin with a sodium chloride gradient at pH 8.4 and omission of the acetic acid/urea wash) which results in retention of most of the isoforms present in the starting material.

Six different preparations of individual isoforms are carried out by preparative isoelectric focusing in a granulated gel bed (Ultrodex, LKB) essentially as per LKB Application Note 198. Pharmalyte (Pharmacia) 2.5–5 ampholytes (Pharmacia) are used and the gel bed contains 5 M urea.

In the first preparation, approximately 20 mg of recombinant erythropoietin in 6.8 ml of 20 mM sodium citrate/100 mM sodium chloride, pH 7.0 are applied to the gel and focused at 8 watts for approximately 16 hours. After isoelectric focusing, the isoform bands in the gel are visualized by a paper contact print of the gel bed. The print is made and then fixed by soaking in 3 changes (approximately 10 minutes each, room temperature) of fixing solution (40% methanol/10% acetic acid/10% TCA/3.5% sulfosalicylic acid), subjected to one change (approximately 10 minutes) of 40% methanol/10% acetic acid (30–60° C.), stained for 15 minutes at 60° C. in 0.125% Coomassie Blue R-250/40% methanol/10% acetic acid, and then destained in 7.5% methanol/10% acetic acid in order to visualize the separated isoforms. The region of the granulated gel bed containing the isoforms (~50% of the resin) is removed, water is added (~16 ml), and the slurry is poured into a 5.5×24.5 inch tray and evaporated to ~40 g net weight. This preparation is focused for a second time and a contact print of the gel bed is made as before. The portion of gel containing each of the six discernible isoforms is removed from the gel bed.

In order to elute the isoforms from the gel, a solution containing 10 mM Tris-HCl, pH 7.0/5 mM Chaps is added to each isoform to generate a slurry. The slurries are placed in small columns and washed with the Tris-Chaps buffer. The flow throughs are collected and applied separately to small columns (open column configuration) containing Vydac C4 reversed phase resin equilibrated in 20% ethanol/10 mM Tris-HCl, pH 7.0. The columns are developed stepwise with 20% ethanol/10 mM Tris-HCl, pH 7.0, 35% ethanol/10 mM Tris-HCl, pH 7.0, and 65% ethanol/10 mM Tris-HCl, pH 7.0. The fraction eluting at 65% ethanol/10 mM Tris is diluted 1:1 with 10 mM Tris-HCl, pH 7.0 and subjected to concentration and then buffer exchanged to 10 mM Tris-HCl, pH 7.0 using a Centricon-10 (Amicon) microconcentrator. Analytical isoelectric focusing of this preparation is performed essentially as described in LKB technical note 250 using Servalyte 3–5 ampholines (Serva) in a polyacrylamide gel containing 5 M urea.

In a second preparation, approximately 26 mg of recombinant erythropoietin in 6.5 ml of deionized water are applied to the gel and focused at 2.5 watts for 35 minutes and 10 watts for approximately 17 hours. The bands of focused protein, which are visible in the gel bed, are removed as 11 different pools. Each pool is brought to about 7.5 ml with deionized water and 20 ml of each of the resulting pool supernatants is subjected to analytical isoelectric focusing as described above. To each of the pools is added 5 ml of 1.5 M Tris-HCl, pH 8.8 and the slurries are each placed in small columns and the liquid phase allowed to flow through. The resin is washed with approximately three volumes of 0.5 M Tris-HCl, pH 7 and the rinse solution is combined with the flow through. The eluants are concentrated and buffer exchanged to 20 mM sodium citrate/100 mM sodium chloride, pH 7.0 using Amicon disposable ultrafiltration devices having a 10,000 dalton molecular weight cutoff. The concentrated solutions (approximately 0.5 ml) are then passed through a 0.22 micron cutoff cellulose acetate filter. Based upon analytical isoelectric focusing, five pools are found to contain predominantly the single isoforms 10, 11, 12, 13 and 14.

In a third preparation, approximately 30 mg of recombinant erythropoietin in 21.8 ml of distilled water is applied to the gel and focused at 2 watts for 25 minutes, 10 watts for 20 hours and 15 watts for 15 minutes. Protein bands corresponding to the individual isoforms are observed visually and removed from the gel bed. Distilled water is added to gel-isolated isoforms to generate a slurry and the resulting supernatants are analyzed by analytical isoelectric focusing. An equal volume of 1 M Tris-HCl, pH 7.2 is added to each slurry, the suspensions are placed into separate small columns, and the liquid phase is allowed to flow through the column to elute the isoforms. Each flow through is concentrated and buffer exchanged to 20 mM sodium citrate/100 mM sodium chloride, pH 7.0 using Amicon disposable ultrafiltration devices having a 10,000 dalton molecular weight cutoff. An analytical isoelectric focusing gel revealed that pools containing predominantly the single isoforms 9, 10, 11, 12, 13 and 14 were obtained.

A fourth isoform preparation used as its starting material erythropoietin containing isoforms 3–9 (prepared as described above). Prior to preparative isoelectric focusing carried out essentially as described for preparations 1–3 above, the ampholytes (Pharmalyte 2.5–5) were pre-fractionated in a Rotofor (Bio-Rad, Richmond, Calif.) liquid phase isoelectric focusing cell to yield an ampholyte range more suitable for the lower isoelectric points of the starting material. The prefractionation was carried out by mixing 6.7 mL of Pharmalyte 2.5–5 with 15 g of urea and adding purified water to bring the volume to 50 mL. This mixture was fractionated in the Rotofor at 10 Watts, 1° C., for 5½ hours using 0.1 M phosphoric acid and 0.1 M sodium hydroxide as the anolyte and catholyte, respectively. The ampholyte fractions having measured pHs of between 4.5 and approximately 6 were used in the flat-bed isoelectric focusing.

Ampholytes were removed from the isoforms using a Centrieluter (Amicon, Danvers, Mass.) and a 10,000 MW cutoff Centricon (Amicon) using the following parameters: 0.18 Tris buffer pH 8.8, 100 Volts, 25–30 mA, for 3 hours. The isoforms were then buffer exchanged into 0.1 M sodium chloride by gel filtration using Sephadex G-25 (Pharmacia). Analytical isoelectric focusing of the five resulting pools showed them to contain isoforms 4,5,6,7, and 8. Isoform 4 ran as several bands, indicating that it may have undergone some degradation.

The fifth isoform preparation was modified by the addition of a pre-focusing step to the flat bed isoelectric focusing procedure. In this modification, the protein was not added to the ampholyte/urea/gel mixture prior to electrophoresis but was added to the isoelectric focusing apparatus following generation of the pH gradient in the gel bed. Following prefocusing for 75 minutes (1500 volt-hrs) the section of gel bed from 2.25–4.25 cm from the cathode was removed, mixed with the erythropoietin solution, and added back to the gel bed. Following isoelectric focusing, isoforms 10,11, 12,13 and 14 were eluted from the gel bed and separated from the ampholytes by ultrafiltration using Centricon-10 (Amicon) devices.

The pre-focusing modification was undertaken to make the ultraviolet absorbance characteristics of the isoform preparations more similar to that of the starting recombinant erythropoietin. This improvement in spectral characteristics can be seen in the ratio of absorbance at 280 and 260 nm for the isolated isoforms. The average ratio of absorbance at 280 nm to that at 260 nm ($A_{280}/A_{260}$) for isoforms from preparations 2 and 3 (non-prefocused) is 1.36±0.11 while the average $A_{280}/A_{260}$ ratio for preparations 5 and 6 (pre-focused) is 1.68±0.20. When isoform #14 is excluded from the calculation, the average $A_{280}/A_{260}$ ratios are 1.39±0.11 and 1.74±0.09 for preparations 2 & 3 and 5 & 6, respectively. (Isoform 14 may have the most atypical spectrum because it is present in the smallest amounts and is thus more subject to interferences by trace contamination by ampholyte components or because it is nearest to the electrode during the flat bed isoelectric focusing procedure). The average $A_{280}/A_{260}$ ratio for recombinant erythropoietin prepared according to Example 2 of Lai et al. (modified as described earlier by using Q-Sepharose as the anion exchange resin) is 1.91±0.04.

As described above, the starting material for isoform preparation #6 was a recombinant erythropoietin preparation containing isoforms 4–13. The ampholytes were pre-focused in the Rotofor apparatus as per the fourth preparation. Ampholyte fractions having measured pHs of between 3.7 and 4.8 were used for the flat bed isoelectric focusing. The flat bed was pre-focused as in run #5 and isoforms 9,10,11, 12 and 13 were obtained after ultrafiltration (Centricon-10) to remove carrier ampholytes.

EXAMPLE 2

Sialic Acid Content of Recombinant Erythropoietin Isoforms

The isoforms isolated as described in Example 1 and erythropoietin purified according to procedures described in Lai et al., supra (mixture of isoforms 9 to 14) are buffer exchanged into 0.10–0.15 M sodium chloride and analyzed for sialic acid content by a modification of the procedure of Jourdian et al. J. Biol. Chem. 246, 430 (1971). The sialic acid residues are cleaved from the glycoproteins by hydrolysis with 0.35 M sulfuric acid at 80° C. for 30 minutes and the solutions are neutralized with sodium hydroxide prior to analysis. In order to estimate the amount of erythropoietin protein present, a Bradford protein assay (Bradford Anal. Biochem. 72, 248 (1976)) using recombinant erythropoietin having the amino acid sequence of human erythropoietin as standard is performed using the assay reagents and the micro-method procedure supplied by Bio-Rad. The results, expressed as moles of sialic acids per mole of erythropoietin, are shown in Table 1. Isoforms are designated according to the number of sialic acids per molecule and range from least acidic (Isoform 9) to most acidic (Isoform 13). Isoforms 9–13 are shown in gel lanes 6–10 of FIG. 1. Quantities of Isoform 14 are insufficient to accurately measure the sialic acid content. The sialic acid content of this isoform is inferred from its migration on IEF gels relative to other isoforms. The sialic acid content of isoforms 5–8 (preparation #4) has not been measured but is likewise inferred from their migration on IEF gels.

TABLE 1

| ERYTHROPOIETIN ISOFORM | MOLES SIALIC ACID/ MOLE ERYTHROPOIETIN |
|---|---|
| Isoform 13 | 12.9 ± 0.5 |
| Isoform 12 | 11.8 ± 0.2 |
| Isoform 11 | 11.0 ± 0.2 |
| Isoform 10 | 9.8 ± 0.3 |
| Isoform 9 | 8.9 ± 0.6 |
| Isoform Mixture (9–14) | 11.3 ± 0.2 |

EXAMPLE 3

Activity of Recombinant Erythropoietin Isoforms

The isoforms isolated as described in Example 1 are assayed by absorbance at 280 nm, by Bradford protein assay and by RIA for erythropoietin to determine the amount of recombinant erythropoietin present. The exhypoxic polycythemic mouse bioassay (Cotes et al. Nature 191, 1065 (1961)) is used to determine the relative in vivo biological activity. Quantitation of the amount of erythropoietin protein present using a radioimmunoassay for erythropoietin produced results having higher relative in vivo specific activity for certain isoforms because of an apparent decreased immunoreactivity of isoforms containing large amounts of sialic acid leading to an underestimation of the erythropoietin concentration and thus an overestimation of the relative in vivo specific activity for the most negative isoforms. Mouse bioassay determinations, expressed as units/ml, are divided by the corresponding protein concentrations to give in vivo specific activities expressed as units/mg erythropoietin polypeptide. These specific activities are shown in Table 2.

In Table 2; "n" is the number of independent isoform preparations which contribute to the specific activity value. In most cases several in vivo assays were performed on each isoform preparation. The same in vivo data contribute to the specific activity calculations for all three columns, units/mg erythropoietin polypeptide was determined by the absorbance at 280 nm, from radioimmunoassay potencies, or from Bradford protein assay results. Purified recombinant erythropoietin containing isoforms 9–14 was used as the standard in the Bradford protein assay. "n" may be less for the calculation made using the Bradford protein assay as some preparations were no longer available at the time the Bradford assays were performed.

Erythropoietin purified according to the procedures described in Lai et al., supra and containing a mixture of isoforms 9 to 14 is used as a standard for the RIAs and in vivo assays.

The relative specific activities expressed as units/mg erythropoietin polypeptide can be converted to units/$A_{280}$ by multiplying by 0.807 mg erythropoietin polypeptide/$A_{280}$. The conversion factor is derived by multiplying the extinction coefficient of erythropoietin (1.345 mg/$A_{280}$) by the protein content of the erythropoietin glycoprotein (about 60% by weight, Davis et al. Biochemistry 26, 2633 (1987)) to obtain mg erythropoietin polypeptide/$A_{280}$ (i.e., 1.345 mg erythropoietin/$A_{280}$×0.60 mg polypeptide/mg erythropoietin=0.807 mg polypeptide/$A_{280}$). In addition, specific activities expressed as units/mg erythropoietin polypeptide can be multiplied by the factor 0.60 mg polypeptide/mg erythropoietin glycoprotein to give specific activities expressed as units/mg erythropoietin glycoprotein.

TABLE 2

| Isoform | U/mG Polypeptide (Bradford Protein Assay) | | n | U/mG Polypeptide (From A280) | | n | U/mG Polypeptide (From RIA) | | n |
|---|---|---|---|---|---|---|---|---|---|
| 14 | 289,400 | 3,100 | 2 | 205,800 | 37,700 | 2 | 366,700 | 55,900 | 2 |
| 13 | 307,600 | 30,600 | 4 | 258,700 | 59,500 | 5 | 337,200 | 40,200 | 5 |
| 12 | 275,200 | 55,600 | 4 | 258,400 | 41,700 | 5 | 287,700 | 42,600 | 5 |
| 11 | 282,700 | 41,100 | 3 | 255,800 | 67,300 | 4 | 251,400 | 62,700 | 4 |
| 10 | 188,000 | 1,900 | 1 | 170,300 | 34,500 | 3 | 171,900 | 31,600 | 3 |
| 9 | — | | | 96,600 | 46,700 | 2 | 113,600 | 39,600 | 2 |
| 8 | 65,200 | 3,800 | 1 | 70,600 | 4,100 | 1 | 61,000 | 3,500 | 1 |
| 7 | 46,200 | 5,800 | 1 | 50,300 | 6,300 | 1 | 42,800 | 5,400 | 1 |
| 5 | 16,600 | 1,700 | 1 | 18,300 | 1,900 | 1 | 15,500 | 1,600 | 1 |

Figure 2A:
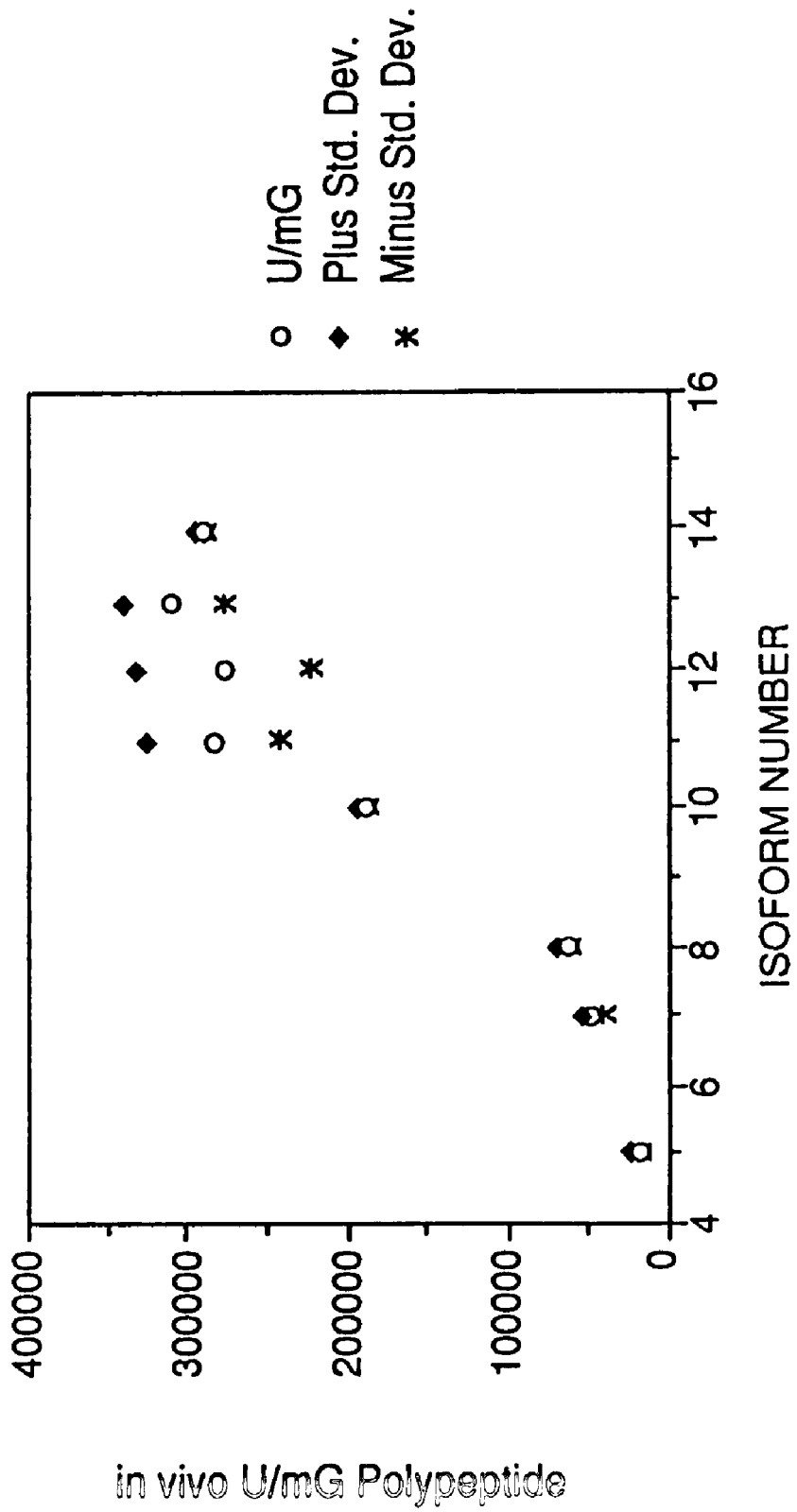
In FIG. 2A, the concentration of each erythropoietin isoform was determined by the Bradford protein assay; in 2B, the concentration was determined by absorbance at 280 nm, in 2C, the concentration was determined by RIA.
Figure 2B:
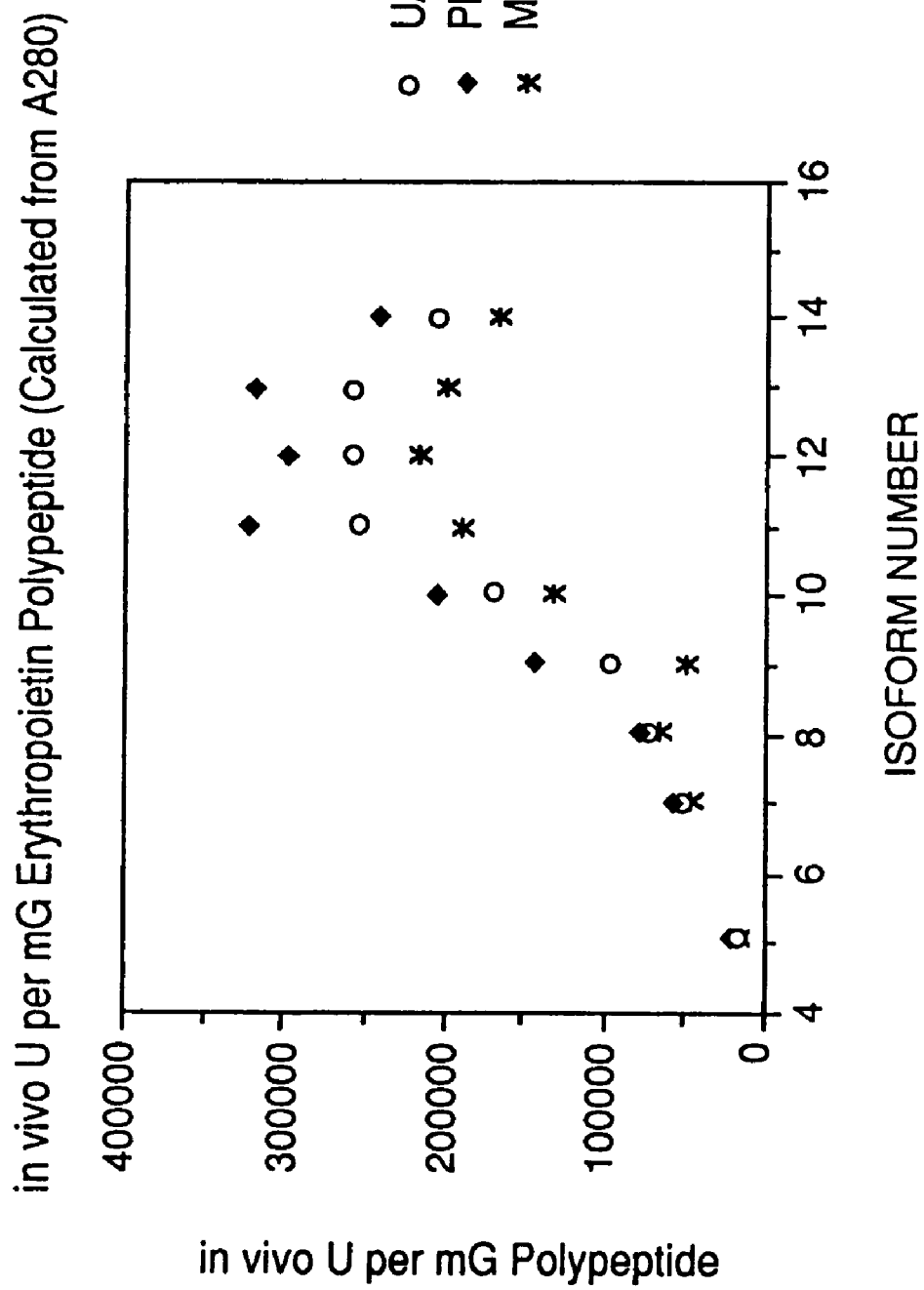
FIG. 2 shows the relationship between the number of sialic acids per erythropoietin isoform and the in vivo specific activity of each isoform expressed as units per mg of erythropoietin polypeptide.
Figure 2C:
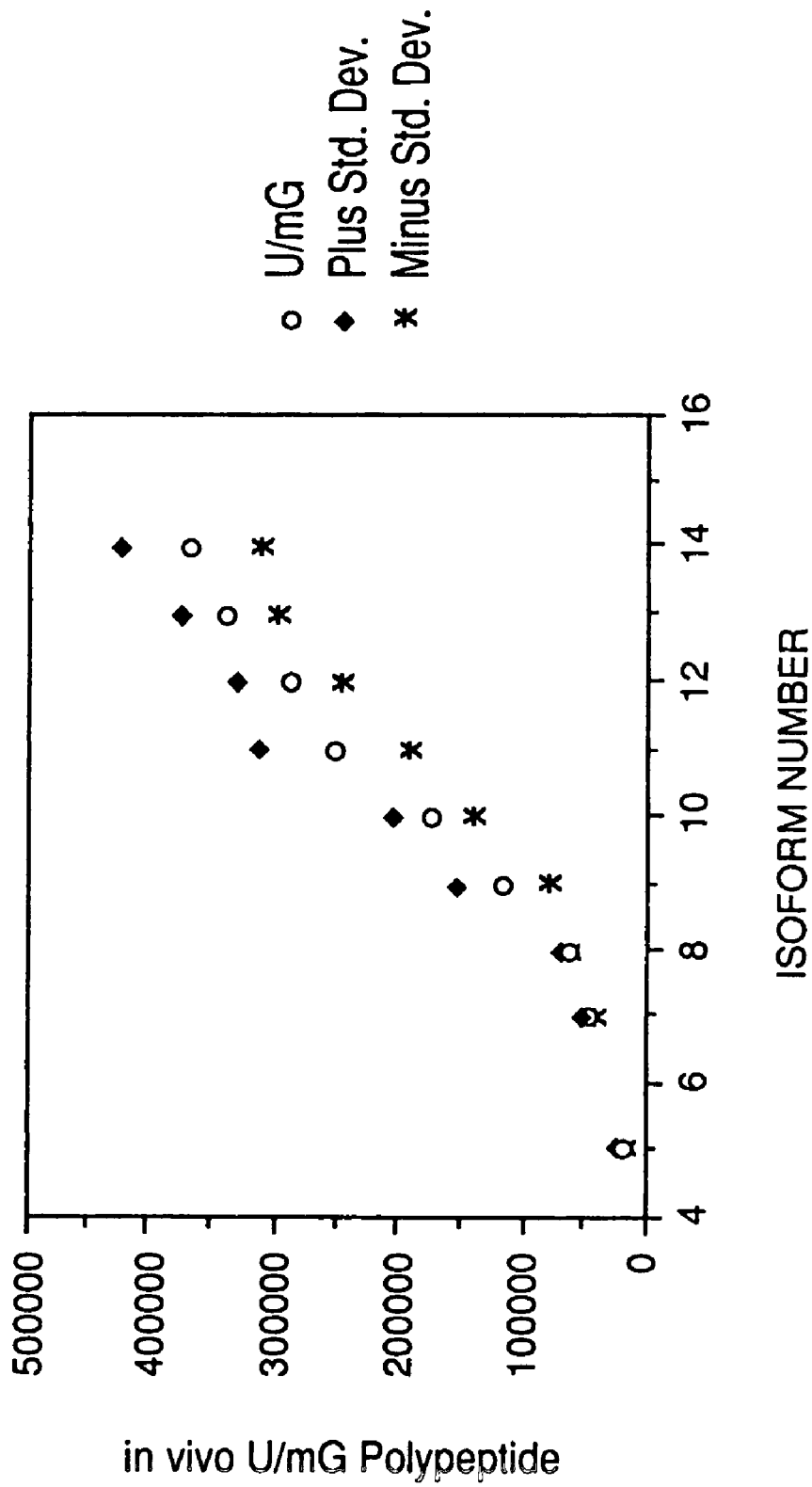

The data in Table 2 are also presented graphically in FIGS. 2A, 2B and 2C. These data show that the relative in vivo activity of erythropoietin increases as a function of sialic acid content up until isoform #11. Isoforms 11–14 have essentially the same relative in vivo bioactivity. (This is most apparent when the concentration of isoform 14 is expressed using the Bradford assay value. The Bradford value may be more accurate for isoform 14 because of the generally low levels obtained and the resulting difficulty in determination by $A_{280}$ and the most apparent decreased reactivity in the RIA of very negative forms discussed previously). The greater relative in vivo specific activity of erythropoietin isoforms having more sialic acid is most likely due to a longer circulating half-life of these forms. Isoforms 9 and 13 were labeled with radioactive iodine ($125_I$) and their rate of clearance in rats was determined. The half-life in circulation was significantly longer for isoform 13 than for isoform 9.

EXAMPLE 4

Selection of Recombinant Erythropoietin Isoform Mixtures by O-Sepharose Chromatography Cell conditioned media from the production of recombinant erythropoietin according to the procedures described in Lin, supra are concentrated and diafiltered against 10 mM Tris, pH 7.2. Protein concentration is determined by the Bradford microprotein assay using bovine serum albumin as a standard. 19.6 ml of the solution containing 40 mg of total protein is made 20 μM in $CuSO_4$, filtered through a 0.45 micron cutoff filter and loaded onto a 4 ml bed volume (1.05 cm height×2.2 cm diameter) column packed with Q Sepharose Fast Flow (Pharmacia) which has been equilibrated with 10 mM Tris, pH 6.8 to 7.0 at 4° C. After sample application, the column is washed with two column volumes of the same buffer. The column flow rate is about 1 ml/min. Six separate columns are set up using this procedure to select defined erythropoietin isoform mixtures.

Columns are washed with 6 to 9 column volumes of a low pH buffer consisting of: Column #1, 150 mM acetic acid, 1 mM glycine, 20 μM $CuSO_4$, 6 M urea adjusted to pH 4.7 with NaOH; Column #2, 200 mM acetic acid, 1 mM glycine, 20 μM $CuSO_4$, 6 M urea adjusted to pH 4.7 with NaOH; Column #3, 250 mM acetic acid, 1 mM glycine, 20 μM $CuSO_4$, 6 M urea adjusted to pH 4.7 with NaOH; Column #4, 300 mM acetic acid, 1 mM glycine, 20 μM $CuSO_4$, 6 M urea adjusted to pH 4.7 with NaOH; Column #5, 150 mM acetic acid, 1 mM glycine, 20 μM $CuSO_4$, 6 M urea; Column #6, 300 mM acetic acid, 1 mM glycine, 20 μM $CuSO_4$, 6 M urea. The pH of the columns is increased to approximately pH 7 by washing each one with 8 to 11 column volumes of 10 mM Tris-HCl, 55 mM NaCl, 20 μM $CuSO_4$, pH 7. The defined erythropoietin isoform mixtures are eluted from the columns by washing with 10 mM Tris-HCl, 140 mM NaCl, 20 μM $CuSO_4$, pH 7.0.

Figure 3:
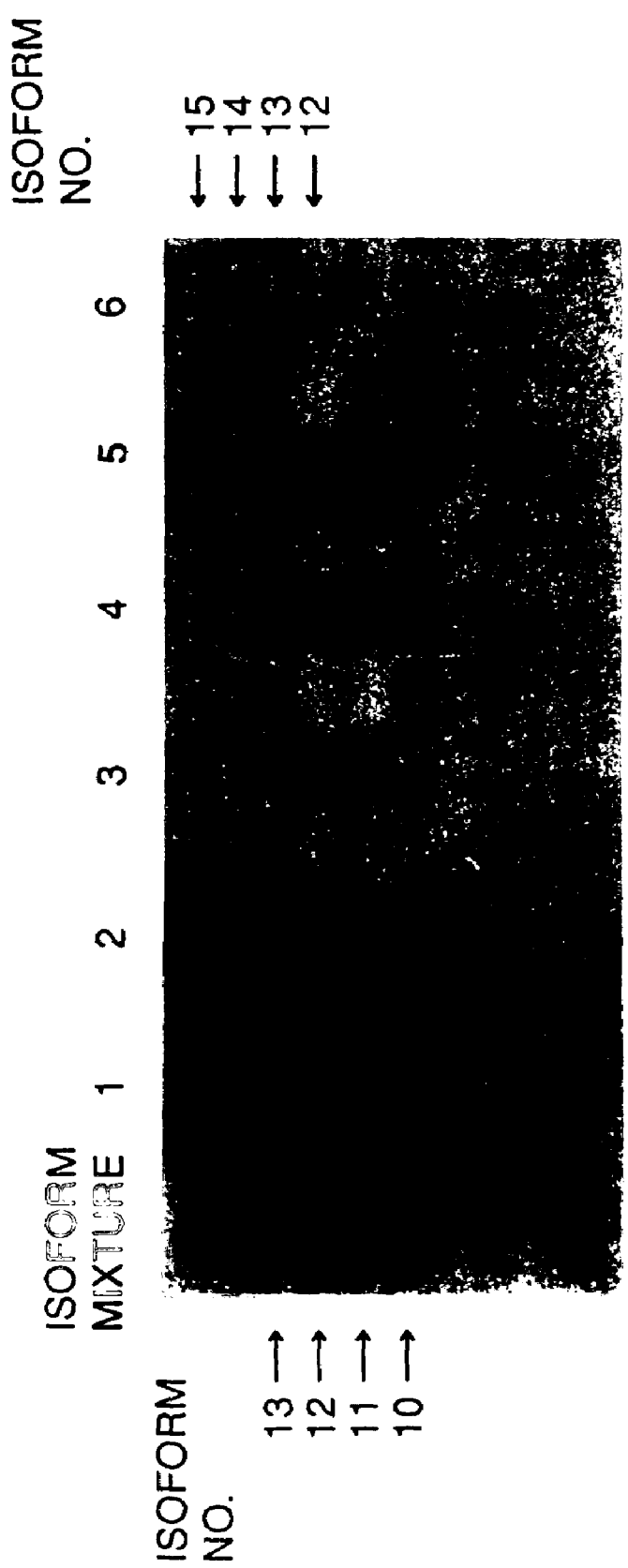
FIG. 3 shows an analytical isoelectric focusing gel of defined mixtures of recombinant erythropoietin isoforms prepared by anion exchange chromatography under different conditions. Gel lanes 1–6 represent, respectively, erythropoietin isoforms eluted in a high salt wash after washing the Q-Sepharose fast flow column with 150 mM acetic acid, pH 4.7, 150 mM acetic acid (unbuffered), 200 mM acetic acid, pH 4.7, 250 mM acetic acid, pH 4.7, 300 mM acetic acid, pH 4.7 or 300 mM acetic acid (unbuffered). Purified recombinant erythropoietin containing a mixture of isoforms as obtained using procedures described in Example 2 of Lai et al., supra, except that DEAE-Agarose chromatography is replaced by Q-Sepharose chromatography, is also shown in the far left lane of the gel.

The eluted isoform pools from each column are concentrated and solvent exchanged into water using an Amicon Centricon-10 microconcentrator. The results of analytical isoelectric focusing of these concentrated pools are shown in FIG. 3. Gel lanes 1–6 represent defined erythropoietin isoform mixtures eluted from column 1–6, respectively. The "isoform mixture" shown in the far right gel lane of FIG. 3 represents cell media which is applied to a Q-Sepharose column as described above, the column is washed with 5 mM acetic acid, 1 mM glycine, 20 μM $CuSO_4$, 6M urea, and the erythropoietin isoform mixture is eluted from the column using the procedures described above. This eluted mixture of isoforms is further purified according to the procedures described in Lai et al., supra prior to analytical isoelectric focusing.

EXAMPLE 5

Figure 4:
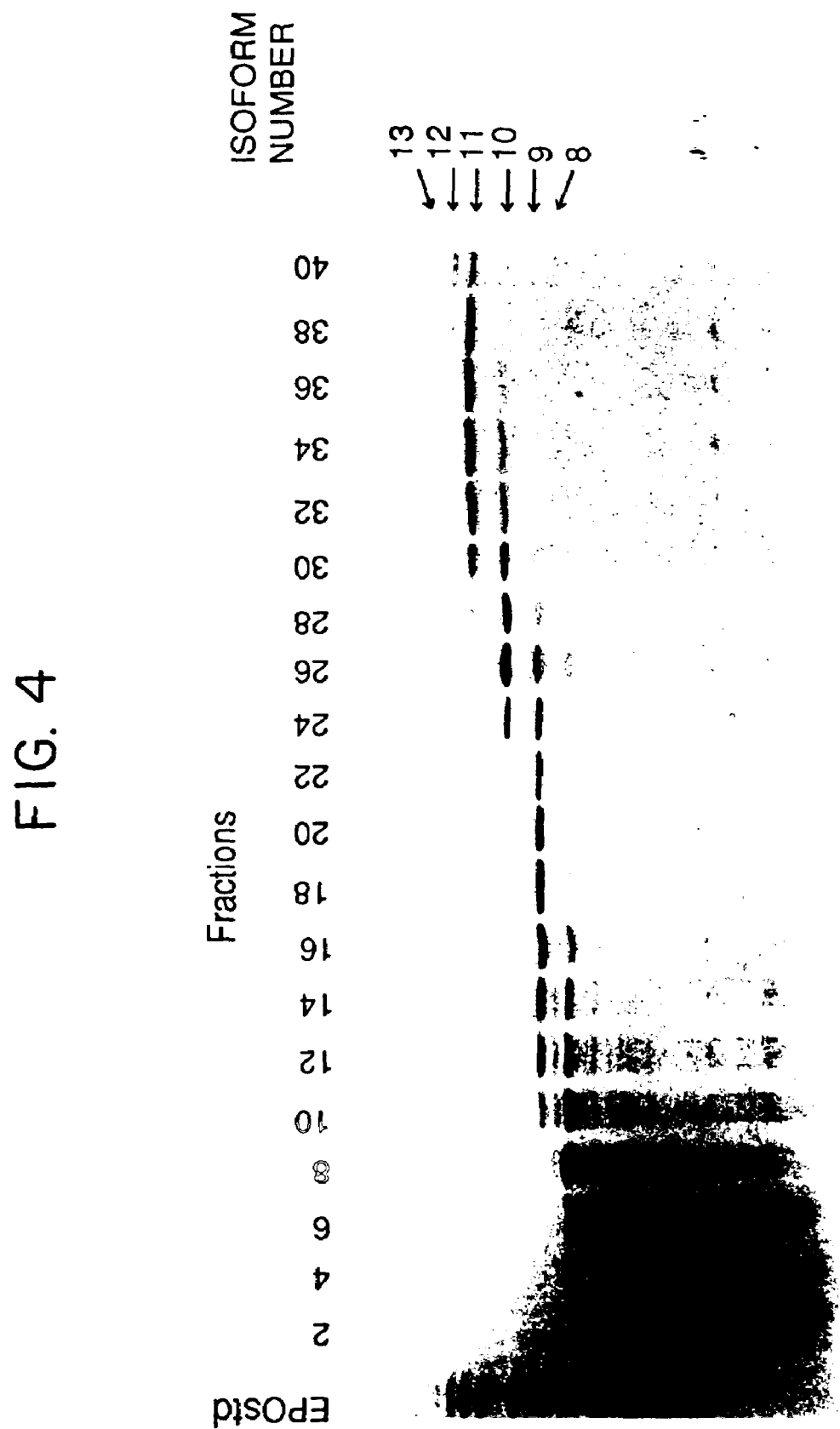
FIG. 4 shows the separation of erythropoietin isoforms 8 to 12 achieved by subjecting cell conditioned medium applied to a column of Q-Sepharose to a gradient of decreasing pH and increasing ionic strength. Aliquots of even numbered fractions from Fraction 2 to Fraction 40 were subjected to analytical isoelectric focusing. Purified recombinant erythropoietin containing a mixture of isoforms obtained using procedures described in Example 2 of Lai et al. supra, except that DEAE-Agarose chromatography is replaced by Q-Sepharose chromatography, is also shown in the far left lane of the gel.

Fractionation of Recombinant Erythropoietin Isoforms Using a Low pH Gradient on O-Sepharose In another procedure, erythropoietin isoforms are separated using a gradient of decreasing pH and increasing ionic strength. The concentrated diafiltered erythropoietin containing media is loaded to a column of Q-Sepharose at a ratio of approximately 40 mg total protein/mL gel. The column is then washed with approximately two column volumes of 10 mM Tris HCl, pH 7.0 and then approximately 10 column volumes of 2 mM acetic acid/1 mM glycine/20 μM $CuSO_4$/6 M urea (pH approximately 4.8) to remove contaminating proteins and erythropoietin isoforms containing less than approximately 7 sialic acid residues. Isoforms containing from approximately 8 to approximately 12 sialic acids are eluted from the column using a gradient starting at approximately 2 mM acetic acid in 6 M urea/1 mM glycine/20 μM $CuSO_4$ and running to 40 mM acetic acid/6 M urea/1 mM glycine/20 μM $CuSO_4$ (pH approximately 4). The total volume of the gradient is approximately 40 column volumes and fractions of approximately one column volume each are collected into vessels containing a volume of Tris buffer sufficient to bring the pH into the range of 6–8.5 so as to avoid long term exposure of the collected fractions to low pH. Aliquots of the fractions are subjected to analytical isoelectric focusing to monitor the separation. FIG. 4 shows the separation of isoforms 8–11 which may be achieved by this procedure. Isoforms 12–14 which remain bound to the column at the end of the gradient are eluted by washing with a buffer consisting of 10 mM TrisHCl, 140 mM NaCl, 20 mM $CuSO_4$ (pH 7.0). The isoforms (separated during the gradient or eluted by the sodium chloride solution) are freed of contaminating proteins by reverse phase chromatography followed by gel filtration chromatography as described in Example 2 of Lai et al.

EXAMPLE 6

Construction of Human Erythropoietin Analogs

Figure 6A:
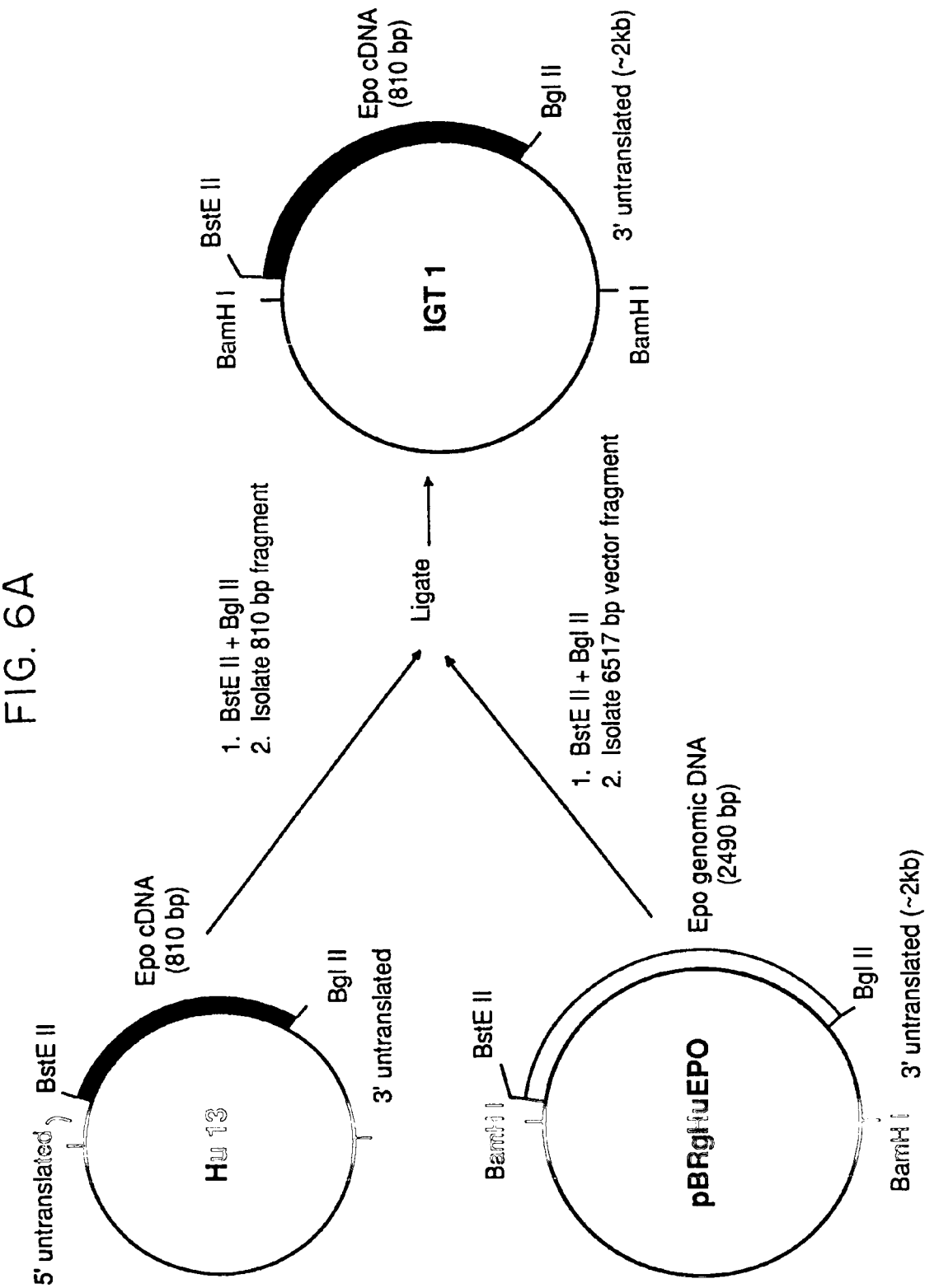
FIGS. 6A, 6B, and 6C show the series of cloning steps used in generating plasmids for the construction and analysis of analogs of human erythropoietin. These analogs have amino acids altered as shown in FIG. 5 which provide additional glycosylation sites.
Figure 6B:
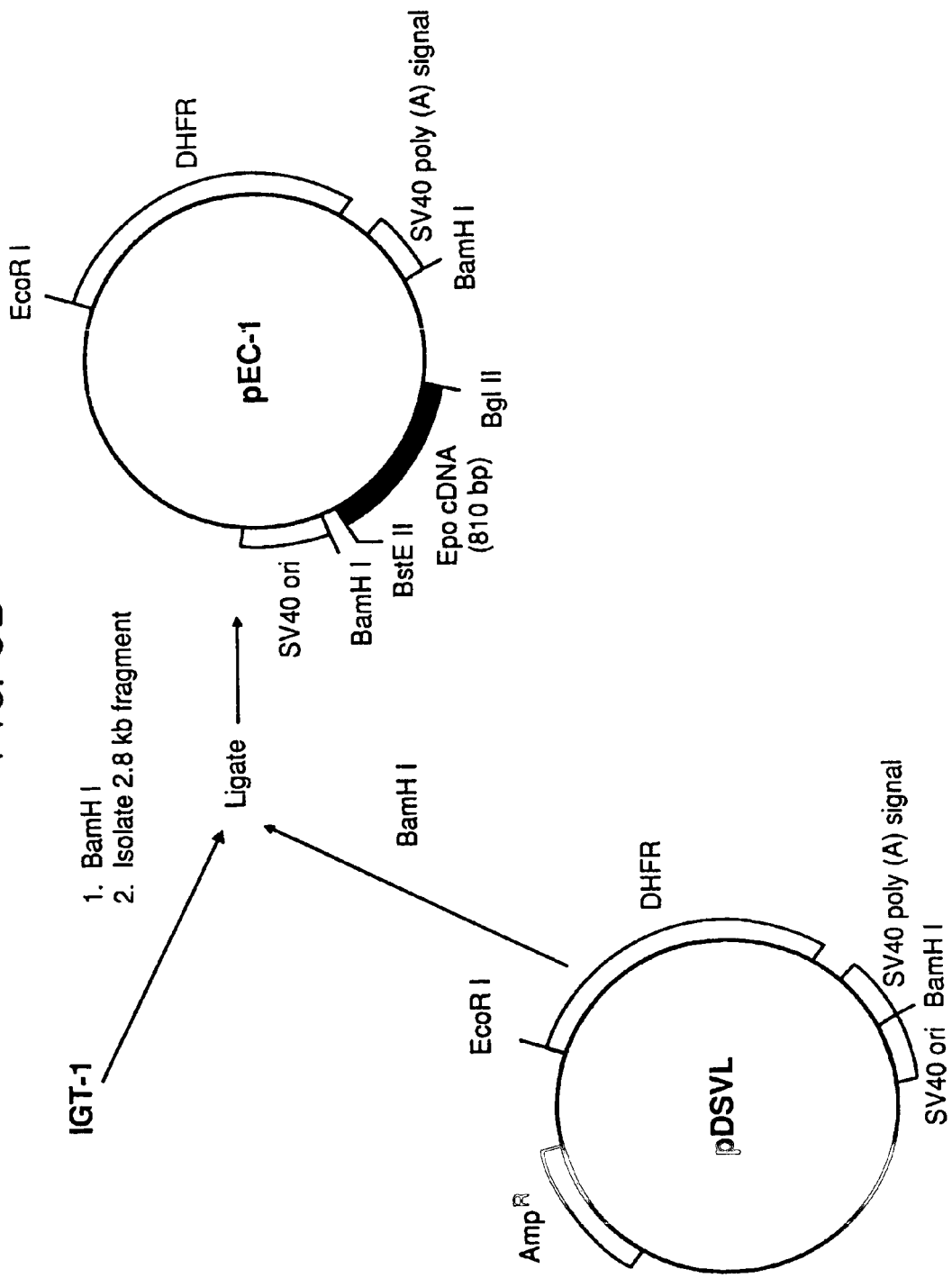
Figure 6C:
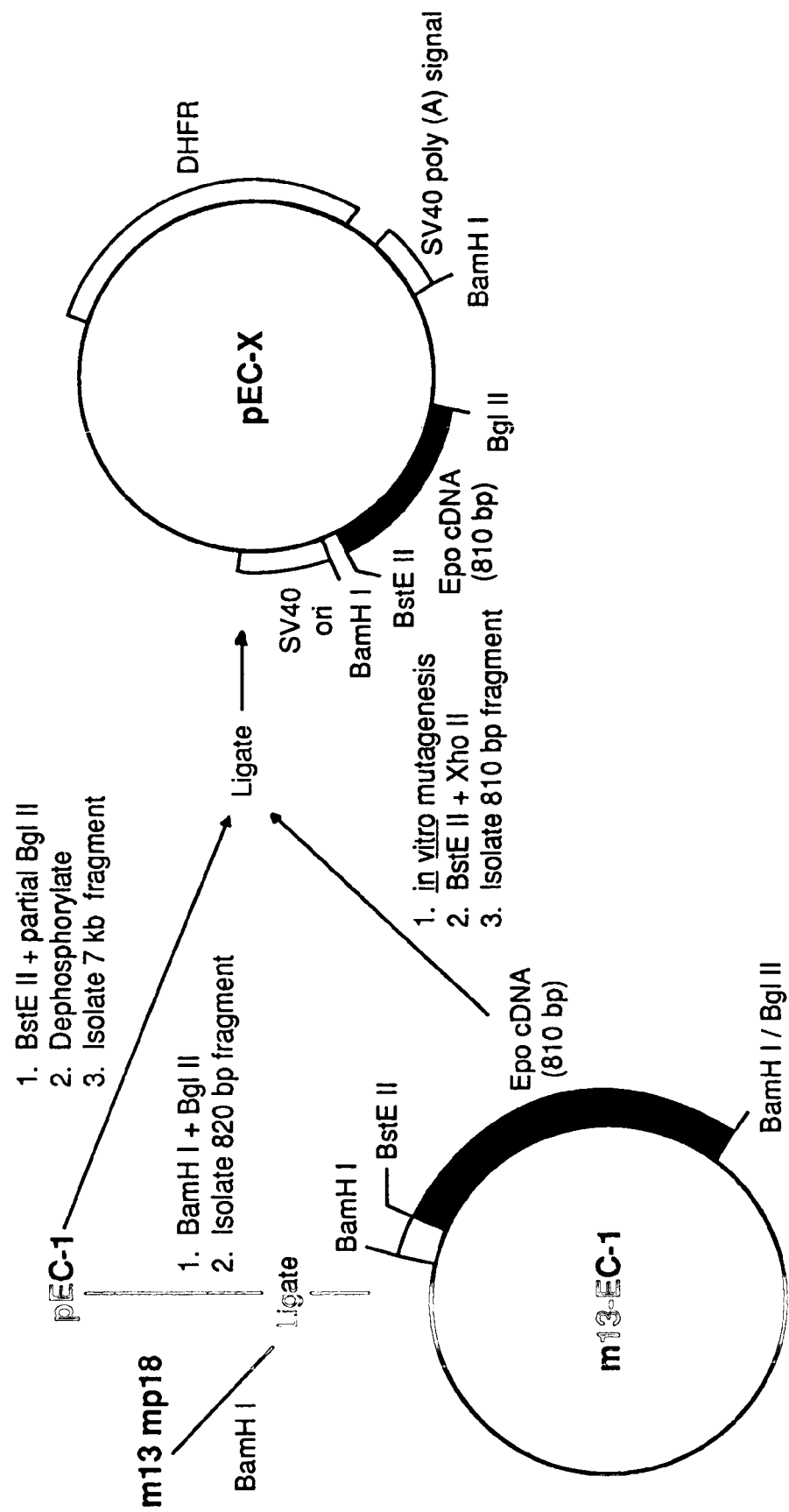

The locations of existing carbohydrate attachment sites within the human erythropoietin amino acid sequence are shown in FIG. 5 (SEQ ID NO: 26). Procedures for generating additional glycosylation sites for erythropoietin are summarized in FIGS. 6A–C and described below.

The following oligonucleotide primers were synthesized for use in in vitro mutagenesis:

```
[Asn⁴, Ser⁶] EPO:                          SEQ ID NO:1
5' CGCCCACCAAACCTCAGCTGTGACAGCCGA 3'

[Asn⁹, Ser¹¹] EPO:                         SEQ ID NO:2
5' ATCTGTACAACCGAAGCCTGGAGAGGT 3'

[Asn⁶⁹] EPO:                               SEQ ID NO:3
5' GGGCCTGGCCAACCTGTCGGAAG 3'

[Asn¹²⁴] EPO:                              SEQ ID NO:4
5' TCCCCTCCAGATAATGCCTCAGCTGC 3'

[Asn¹²⁵, Ser¹²⁷] EPO:                      SEQ ID NO:5
5' CAGATGCGAACTCATCTGCTCCAC 3'

[Asn¹⁶³, Ser¹⁶⁵] EPO:                      SEQ ID NO:6
5' AGGCCTGCAGGAATGGGAGCAGATGACCAGGTG 3'

[Thr¹²⁵] EPO:                              SEQ ID NO:7
5' TCCAGATGCGACCTCAGCTGCTC 3'

[Pro¹²⁴, Thr¹²⁵] EPO:                      SEQ ID NO:8
5' CCTCCAGATCCGACCTCAGCTGC 3'
```

The underlined codons show the mismatched regions where the amino acids indicated in brackets replace the wild-type amino acids.

[Asn⁴, Ser⁶] EPO was constructed to add an N-glycosylation site at Asn 4. [Asn⁹, Ser¹¹] EPO was constructed to add an N-glycosylation site at Asn 9. [Asn⁶⁹] EPO was constructed to add an N-glycosylation site at Asn 69. [Asn¹²⁵, Ser¹²⁷] EPO was constructed to add an N-glycosylation site at Asn 125. [Thr¹²⁵] EPO and [Pro¹²⁴, Thr¹²⁵] EPO were constructed to add an O-glycosylation site at Thr 125.

The following oligonucleotide primers were synthesized for use in in vitro mutagenesis:

```
[Asn⁶⁹, Thr⁷¹] EPO:                        SEQ ID NO:9
5' GGGCCTGGCCAACCTGACAGAAGCTGTC 3'

[Ser⁶⁸, Asn⁶⁹, Thr⁷¹] EPO:                 SEQ ID NO:10
5' CAGGGCCTGTCCAACCTGACAGAAGCTGTC 3'
```

-continued
```
[Asn¹²⁵, Thr¹²⁷] EPO:                      SEQ ID NO:11
5' CAGATGCGAACTCAACGGCTCCAC 3'

[Asn¹²⁵, Thr¹²⁷, Thr¹³¹] EPO:              SEQ ID NO:12
5' ATGCGAACTCAACGGCTCCACTCACAACAATCACT 3'

[Pro¹²⁴, Asn¹²⁵, Ser¹²⁷] EPO:              SEQ ID NO:13
5' CCAGATCCAAATTCATCTGCTCCACTC 3'

[Pro¹²⁴, Asn¹²⁵, THr¹²⁷] EPO:              SEQ ID NO:14
5' CCAGATCCAAATTCAACAGCTCCACTC 3'

[Thr¹²⁵, Thr¹²⁶] EPO:                      SEQ ID NO:15
5' CCAGATGCGACAACAGCTGCTCCA 3'
```

[Pro¹²⁴, Thr¹²⁵, Thr¹²⁶, Thr¹³¹] EPO:

Starting from [Pro¹²⁴, Thr¹²⁵] EPO cDNA, the oligonucleotide primer 5' AGATCCGACCACCGCTGCTCCAC 3' SEQ ID NO. 16 is used to generate [Pro¹²⁴, Thr¹²⁵, Thr¹²⁶] EPO. The oligonucleotide primer 5'TGCTCCACTCAAACAATCACTG 3' SEQ ID NO: 17 is then used to generate [Pro¹²⁴, Thr¹²⁵, Thr¹²⁶, Thr¹³¹] EPO.

[Asn⁶⁹, Thr⁷¹] EPO and [Ser⁶⁸, Asn⁶⁹, Thr⁷¹] EPO are constructed to add an N-glycosylation site at Asn 69 and to enhance N-glycosylation at that site. [Asn¹²⁵, Thr¹²⁷] EPO, [Asn¹²⁵, Thr¹²⁷, Thr¹³¹] EPO, [Pro¹²⁴, Asn¹²⁵, Ser¹²⁷] EPO and [Pro¹²⁴, Asn¹²⁵, Thr¹²⁷] EPO are constructed to add an N-glycosylation site at Asn 125 and to increase glycosylation at that site. [Thr¹²⁵, Thr¹²⁶] EPO and [Pro¹²⁴, Thr¹²⁵, Thr¹²⁶, Ser¹³¹] EPO are constructed to add an O-glycosylation site at Thr 125 and to increase glycosylation at that site.

The source of erythropoietin DNA for in vitro mutagenesis was plasmid Hu13, a human erythropoietin cDNA clone in pUC 8 (Law et al. Proc Natl. Acad. Sci. 83, 6920 (1986)). Plasmid DNA derived from Hu13 was digested with BstEII and BglII restriction enzymes, the resulting DNA fragments were subjected to agarose gel electrophoresis, and the 810 base pair (bp) erythropoietin DNA fragment was isolated from the gel using a GeneClean™ kit and procedures supplied by the manufacturer (BIO 101, Inc.). Plasmid pBRgHuEPO contains the erythropoietin genomic gene as a BamHI fragment inserted into a derivative of pBR322, as described in commonly owned Lin patent, supra, pBR-gHuEPO was also digested with BstEII and BglII and the 6517 bp vector fragment was recovered. Ligation of the two fragments results in IGT1. To construct pEC-1, pDSVL (described in commonly owned Lin patent, supra, and shown in FIG. 6B) was digested with BamHI and the isolated 2.8 kilobase (kb) BamHI fragment from IGT1 containing erythropoietin cDNA was ligated into it.

In order to generate single-stranded DNA for in vitro mutagenesis, pEC-1 was digested with BamHI and BglII and the 820 bp erythropoietin cDNA fragment was isolated. It was ligated into the BamHI site of m13mp18 to give m13-EC-1. Single stranded DNA was recovered from supernatants of *E. coli* strain RZ1032 infected by m13-EC-1 as described by Kunkel et al. Methods in Enzymol. 154, 367 (1987) and Messing, Methods in Enzymol. 101, 20 (1983). For in vitro mutagenesis approximately 1 µg of single-stranded DNA and 0.2 pmole of one of the synthetic primers described above were mixed with 6 µl of buffer (250 mM Tris pH 7.8, 50 mM $MgCl_2$, and 50 mM dithiothreitol). For annealing of the primer to the template, the reaction volume was adjusted to 10 µl with water, the mixture was heated to 65° C. for 5 minutes and then allowed to cool to room temperature. For the elongation reaction 2.5 µl of each of dTTP, dATP, dGTP, dCTP and ATP (all at 10 µM) were added, followed by 1 µl (1 unit) of E. coli DNA polymerase (Klenow fragment) and 1 µl (1 unit) of T4 DNA ligase. The mixture was then incubated overnight at 14° C. and used to transform E. coli JM 109 (Yanisch-Perron et al. Gene 33, 103 (1985)) as described (Messing, supra).

To identify mutant clones by differential hybridization, plaques on nutrient agar were transferred to Gene Screen filters (New England Nuclear). The filters were dried under a heat lamp and then incubated for one hour in 6×SSC containing 1% SDS at 60° C. For the hybridization, the oligonucleotide primer above (8 pmoles) was end-labeled with T4 polynucleotide kinase and γ $^{32}$P-labeled ATP and incubated with the filters overnight in 6×SSC, 0.5% SDS and 100 mg/ml salmon sperm DNA at 37° C. for the [Asn$^{124}$] mutation, 55° C. for the [Asn$^{4}$, Ser$^{6}$] mutation, 65° C. for the [Thr$^{125}$] and the [Pro$^{124}$, Thr$^{125}$] mutations, and 70° C. for the [Asn$^{9}$, Ser$^{11}$] and [Asn$^{163}$, Ser$^{165}$] mutations. The next day, the filters were washed three times with 6×SSC at room temperature and subjected to autoradiography. If necessary, the filters were then washed with 6×SSC at increasing temperatures until little or no hybridization was detected to plaques having the wild-type erythropoietin cDNA sequence. Clones that gave positive hybridization signals under these conditions were identified and retransfected into JM109 to isolate a pure clone. Dideoxy chain termination sequence analysis indicated that the mutations to asparagine, serine threonine and proline residues were present.

Double stranded m13 EC-1 DNAs carrying the [Asn$^{4}$, Ser$^{6}$], [Asn$^{9}$, Ser$^{11}$], [Asn$^{69}$], [Asn$^{124}$], [Asn$^{125}$], [Ser$^{127}$], [Asn$^{163}$, Ser$^{165}$] [Thr$^{125}$], and [Pro$^{124}$, Thr$^{125}$] changes were recovered from JM109 transfected cells by the boiling method (Holmes et al. Anal. Biochem 117, 193 (1981)). The DNAs were digested with BstEII and XhoII and the 810 bp erythropoietin DNA fragments were isolated. pEC-1 was digested with BstEII followed by a partial digestion with BglII and the 5' termini of the resulting fragments are dephosphorylated with bacterial alkaline phosphatase in 10 mM Tris, pH 8 at 60° C. for 60 minutes. The 7 kb vector fragment lacking the 810 bp BstEII-BglII fragment was isolated and ligated to the erythropoietin fragments above. The resulting plasmids (designated pEC-X where X is the analog number) contain DNA encoding erythropoietin analogs having altered amino acid residues at the indicated positions.

Alternatively, an analog of erythropoietin (pEC34) was constructed by in vitro mutagenesis that deleted amino acid residues 41–55. This resulted in a smaller (775 bp) EPO containing BstEII-BglII fragment. The fragment was inserted into pEC1 as described above. For cloning analogs of erythropoietin, pEC34 was digested with BstEII, partially digested with BglII, dephosphorylated and the vector isolated as described above. The 7 kb vector fragment was then ligated to erythropoietin fragments as described above. Cloning with pEC34 allows easy discrimination between recombinants and simple reclosures. Reclosures result in a smaller BstEII-BglII fragment than analogs and these can be easily differentiated on agarose gels.

These general procedures were used to construct the erythropoietin analogs shown in Tables 3, 4 and 5. The DNA sequence changes for each of the analogs are shown; otherwise the oligonucleotide primers used for mutagenesis had sequences complimentary to those of human erythropoietin.

TABLE 3

ERYTHROPOIETIN ANALOGS HAVING SITES FOR N-LINKED CARBOHYDRATE CHAINS

| Analog No. | Amino Acid Substitution | Sequence Changes |
|---|---|---|
| N1 | Asn$^{4}$Ser$^{6}$ | CGC→AAC ATC→AGC |
| N2 | Asn$^{9}$Ser$^{11}$ | AGC→AAC GTC→AGC |
| N3 | Asn$^{19}$Thr$^{21}$ | GCC→AAC GAG→ACG |
| N4 | Asn$^{30}$Thr$^{32}$ | GCT→AAT CAC→ACG |
| N5 | Asn$^{42}$ | CCA→AAT |
| N6 | Ser$^{42}$Asn$^{43}$Thr$^{45}$ | CCA→TCA GAC→AAC AAA→ACA |
| N7 | Ser$^{49}$ | TAT→TCT |
| N8 | Asn$^{51}$Thr$^{53}$ | TGG→AAT AGG→ACG |
| N9 | Asn$^{57}$Thr$^{59}$ | GGG→AAC CAG→ACG |
| N10 | Asn$^{69}$ | CTG→AAC |
| N11 | Asn$^{69}$Thr$^{71}$ | CTG→AAC TCG→ACA |
| N12 | Ser$^{68}$Asn$^{69}$Thr$^{71}$ | N11 plus GCC→TCC |
| N13 | Asn$^{88}$Thr$^{90}$ | TGG→AAT CCC→ACC |
| N14 | Ser$^{87}$Asn$^{88}$Thr$^{90}$ | N13 plus CCG→TCG |
| N15 | Ser$^{87}$Asn$^{88}$Thr$^{90}$Thr$^{92}$ | N14 plus CAG→ACG |
| N16 | Ser$^{87}$Asn$^{88}$Thr$^{90}$Ala$^{162}$ | N14 plus AGG→GCG |
| N17 | Asn$^{88}$Ser$^{90}$ | TGG→AAT CCC→TCC |
| N18 | Val$^{87}$Asn$^{88}$Thr$^{90}$ | CCG→GTG TGG→AAT CCC→ACC |
| N19 | Ser$^{87}$Asn$^{88}$Gly$^{89}$Thr$^{90}$ | CCG→TCG TGG→AAT GAG→GGG CCC→ACC |
| N20 | Asn$^{89}$Ile$^{90}$Thr$^{91}$ | GAG→AAC CCC→ATC CTG→ACG |
| N21 | Ser$^{87}$Asn$^{89}$Ile$^{90}$Thr$^{91}$ | N20 plus CCG→TCG |
| N22 | Asn$^{113}$Thr$^{115}$ | GGA→AAC CAG→ACG |
| N23 | Asn$^{118}$Val$^{121}$ | GCC→AAC CCT→GTT |
| N24 | Asn$^{121}$Ser$^{122}$Thr$^{123}$ | CCT→AAT CCA→TCA GAT→ACT |
| N25 | Asn$^{124}$ | GCG→AAT |
| N26 | Ser$^{122}$Asn$^{124}$ | CCA→TCA GCG→AAC |
| N27 | Asn$^{125}$Ser$^{127}$ | GCC→AAC GCT→TCT |
| N28 | Asn$^{125}$Thr$^{127}$ | GCC→AAC GCT→ACG |
| N29 | Leu$^{121}$Ser$^{122}$Asn$^{125}$Thr$^{127}$ | N28 plus CCT→CTT CCA→TCA |
| N30 | Thr$^{120}$Gly$^{122}$Leu$^{123}$Asn$^{125}$Thr$^{127}$ | N28 plus TCC→ACC CGC→GGG GAT→CTC |
| N31 | Asn$^{126}$Ser$^{128}$ | TCA→AAT GCT→TCT |
| N32 | Asn$^{126}$Thr$^{128}$Val$^{129}$ | TCA→AAT GCT→ACT CCA→GTA |
| N33 | Leu$^{121}$Ser$^{122}$Asn$^{126}$Thr$^{128}$Val$^{129}$ | N32 plus CCT→CTT CCA→TCA |

TABLE 3-continued

ERYTHROPOIETIN ANALOGS HAVING SITES FOR N-LINKED CARBOHYDRATE CHAINS

| Analog No. | Amino Acid Substitution | Sequence Changes |
|---|---|---|
| N34 | Thr$^{121}$Gly$^{123}$Ser$^{125}$Asn$^{126}$Thr$^{128}$Val$^{129}$ | N32 plus CCT→ACG GAT→GGG GCC→TCC |
| N35 | Ser$^{129}$Asn$^{130}$ | CCA→AGC CTC→AAC |
| N36 | Asn$^{132}$ | ACA→AAC |
| N37 | Asn$^{134}$Thr$^{136}$ | ACT→AAT GAC→ACC |
| N38 | Asn$^{135}$ | GCT→AAT |
| N39 | Asn$^{136}$Thr$^{138}$ | GAC→AAC TTC→ACC |
| N40 | Asn$^{137}$Thr$^{139}$ | ACT→AAT CGC→ACC |
| N41 | Asn$^{138}$Thr$^{140}$ | TTC→AAC AAA→ACA |
| N42 | Asn$^{144}$ | GTC→AAC |
| N43 | Ser$^{143}$Thr$^{149}$Val$^{150}$ | TTC→TCC CTC→ACC CGG→GTG |
| N44 | Gly$^{148}$Thr$^{149}$ | TTC→GGC CTC→ACC |
| N45 | Asn$^{155}$ | CTG→AAT |
| N46 | Asn$^{163}$Ser$^{165}$ | ACA→AAT |
| N47 | Asn$^{30}$Thr$^{32}$Val$^{87}$Asn$^{88}$Thr$^{90}$ | N4 and N18 |
| N48 | Asn$^{69}$Thr$^{71}$Ser$^{87}$Asn$^{88}$Thr$^{90}$ | N11 and N14 |

TABLE 4

ERYTHROPOIETIN ANALOGS HAVING SITES FOR O-LINKED CARBOHYDRATE CHAINS

| Analog No. | Amino Acid Substitution | Sequence Change |
|---|---|---|
| O1 | Ser$^6$ | ATC→AGC |
| O2 | Ser$^7$ | TGT→TCC |
| O3 | Ser$^8$ | GAC→AGC |
| O4 | Ser$^{11}$ | GTC→TCT |
| O5 | Ser$^{18}$ | CAG→TCG |
| O6 | Ser$^{23}$ | GAG→TCG |
| O7 | Ser$^{29}$ | TGT→AGC |
| O8 | Ser$^{29}$ | TGT→TCT |
| O9 | Ser$^{30}$ | GCT→TCT |
| O10 | Ser$^{33}$ | TGC→TCA |
| O11 | Ser$^{37}$ | GAG→TCG |
| O12 | Ser$^{49}$ | TAT→TCT |
| O13 | Ser$^{61}$ | GTA→TCA |
| O14 | Ser$^{63}$ | GTC→TCC |
| O15 | Ser$^{67}$ | CTG→TCG |
| O16 | Ser$^{68}$ | GCC→TCC |
| O17 | Ser$^{70}$ | CTG→TCG |
| O18 | Ser$^{73}$ | GCT→TCT |
| O19 | Ser$^{74}$ | GTC→TCT |
| O20 | Ser$^{75}$ | CTG→TCG |
| O21 | Ser$^{79}$ | GCC→TCC |
| O22 | Ser$^{81}$ | TTG→TCG |
| O23 | Ser$^{86}$ | CAG→TCG |
| O24 | Ser$^{87}$ | CCG→TCG |
| O25 | Ser$^{93}$ | CTG→TCG |
| O26 | Ser$^{98}$ | GCC→TCC |
| O27 | Ser$^{99}$ | GTC→TCC |
| O28 | Ser$^{102}$ | CTT→TCT |
| O29 | Ser$^{103}$ | CGC→AGT |
| O30 | Ser$^{105}$ | CTC→AGC |
| O31 | Ser$^{109}$ | CTT→TCT |
| O32 | Ser$^{111}$ | GCT→TCT |
| O33 | Ser$^{112}$ | CTG→TCG |
| O34 | Ser$^{114}$ | GCC→TCC |
| O35 | Ser$^{128}$ | GCT→TCT |

TABLE 4-continued

ERYTHROPOIETIN ANALOGS HAVING SITES FOR O-LINKED CARBOHYDRATE CHAINS

| Analog No. | Amino Acid Substitution | Sequence Change |
|---|---|---|
| O36 | Ser$^{159}$ | TCG→GAG |
| O37 | Ser$^{161}$ | TGC→TCC |
| O38 | Pro$^{125}$Ser$^{127}$ | GCC→CCC GCT→TCT |
| O39 | Thr$^{62}$ | GAA→ACA |
| O40 | Thr$^{64}$ | TGG→ACG |
| O41 | Thr$^{65}$ | CAG→ACG |
| O42 | Thr$^{88}$ | TGG→ACG |
| O43 | Thr$^{90}$ | CCC→ACC |
| O44 | Thr$^{92}$ | CAG→ACG |
| O45 | Thr$^{100}$ | AGT→ACT |
| O46 | Thr$^{110}$ | CGG→ACG |
| O47 | Thr$^{115}$ | CAG→ACG |
| O48 | Thr$^{123}$ | GAT→ACT |
| O49 | Thr$^{124}$ | GCG→ACG |
| O50 | Thr$^{125}$ | GCC→ACC |
| O51 | Thr$^{125}$Ser$^{127}$ | GCC→ACC GCT→TCT |
| O52 | Thr$^{125}$Thr$^{126}$ | GCC→ACA TCA→ACA |
| O53 | Thr$^{126}$ | TCA→ACC |
| O54 | Thr$^{127}$ | GCT→ACT |
| O55 | Thr$^{130}$ | CTC→ACC |
| O56 | Thr$^{131}$ | CGA→ACA |
| O57 | Thr$^{136}$ | GAC→ACC |
| O58 | Thr$^{140}$ | AAA→ACA |
| O59 | Pro$^{124}$Thr$^{125}$ | GCG→CCG GCC→ACC |
| O60 | Pro$^{124}$Thr$^{125}$Thr$^{126}$ | O59 plus TCA→ACC |
| O61 | Pro$^{124}$Thr$^{125}$Thr$^{126}$Thr$^{131}$ | O60 plus CGA→ACA |
| O62 | HCG C-terminal extension | |

TABLE 5

ERYHROPOIETIN ANALOGS HAVING SITES FOR N- AND O-LINKED CARBOHYDRATE CHAINS

| Analog No. | Amino Acid Substitution | Sequence Change |
|---|---|---|
| NO1 | Ser$^{87}$Asn$^{88}$Thr$^{90}$ HCG C-terminal extension | N14 and O62 |
| NO2 | Asn$^{30}$Thr$^{32}$Val$^{87}$Asn$^{88}$Thr$^{90}$ HCG C-terminal extension | N47 and O62 |

Plasmids designated pDEC-X (where X is the analog number) were constructed by inserting erythropoietin cDNA into pDECΔ, which is a derivative of plasmid pDSα2. The expression vector pDSα2 is generally described in PCT Application No. WO 90/14363. pDECΔ was derived from pDSα2 by the following steps:

(1) The HindIII site of pDSα2 was deleted by digesting pDSα2 DNA with HindIII, treating the HindIII cohesive ends with *E. coli* DNA Polymerase (Klenow fragment) and dNTPs, and religating the blunt-ended vector. The resulting plasmid was pDSα2ΔH.

(2) pDSα2ΔH was digested with SalI and a synthetic oligonucleotide having an SV40 splice signal with a SalI linker attached to the 3' end of the splice signal was ligated to it. The synthetic oligonucleotide had the following sequence SEQ ID NO: 18

```
5' TCGAGGAACTGAAAAACCAGAAAGTTAACTGGTAAGTTTAGT
CTTTTTGTCTTTTATTTCAGGTCCCGGATCCGGTGGTGGTGCAAATCA
AAGAACTGCTCCTCAGTGGATGTTGCCTTTACTTCTAGGCCTGTACGG
AAGTGTTACTTCTGCTCTAAAAGCTGCTGCAACAAGCTGGTCGACC 3'
```

The resulting plasmid was pDSα2ΔH splice.

3) pDSα2ΔH splice was digested with SalI and blunt-ended by treating the cohesive ends with T4 DNA polymerase and dNTPs. An 820 bp. BamHI-BglII human erythropoietin cDNA fragment was blunt-ended by the same method and ligated to the plasmid. The resulting plasmid was pDEC-1.

4) pDEC was digested with KpnI and PvuII and blunt-ended by treating the cohesive ends with mung bean nuclease. The plasmid was religated to delete the excised KpnI-PvuII fragment resulting in the plasmid pDECΔ.

pDEC-X plasmids were made from pDECΔ by complete digestion with BstEII followed by a partial digestion with BglII. The vector fragment lacking erythropoietin coding sequences was isolated and ligated to the 810 bp BstEII-BglII fragments containing the desired plasmid.

Details of the construction of some analogs having multiple amino acid changes are described below.

Construction of pDEC(N47) and pDEC(N48)

pDEC(N47) which contains asn30 thr32 val87 asn88 and thr90 mutations was constructed from pDEC(N18) and pDEC(N4). pDEC(N18) was digested with HindIII and BglII and a 445 bp fragment was isolated. pDEC(N4) was digested with BstEII and HindIII and a 377 bp fragment was isolated. These two fragments were ligated into pDECΔ cut with BstEII and BglII as described above resulting in pDEC(N47).

pDEC(N48) which contains asn69 thr71 ser87 asn88 and thr90 mutations was constructed from pDEC(N14) and pDEC(N11). pDEC(N14) was digested with HindIII and BglII and a 445 bp fragment was isolated. pDEC(N11) was digested with BstEII and HindIII and a 377 bp fragment was isolated. These two fragments were ligated into pDECΔ cut with BstEII and BglII as described above resulting in pDEC(N48).

Construction of pDEC(O62) (HCG-Erythropoietin Fusion)

pDEC(O62) was assembled from pEC1 and a 107 base pair StuI-BglII synthetic DNA linker containing the carboxy terminal 28 amino acids from human chorionic gonadotropin (ser-ser-ser-ser-lys-ala-pro-pro-pro-ser-leu-pro-ser-pro-ser-arg-leu-pro-gly-pro-ser-asp-thr-pro-ile-leu-pro-gln SEQ ID NO: 25) (Pierce et al. Ann. Rev. Biochem. 50, 465 (1981)). The sequence of the linker is as follows:

pEC1 was digested with StuI and BglII and the 610 bp DNA fragment was isolated. The synthetic linker was phosphorylated with ATP and polynucleotide kinase and ligated with the pEC1 fragment into pDECΔ previously digested with BstEII and partially digested with BglII as described above.

Construction of pDEC(NO1)

pDEC(NO1) was assembled from pDEC(O62)(HCG-EPO) and pDEC(N14) ($Ser^{87}Asn^{88}Thr^{90}$). pDEC177 was digested with StuI and BglII and the 610 bp DNA fragment containing the $Ser^{87}Asn^{88}Thr^{90}$ mutations was isolated with gene-clean. pDEC(O62) was digested with StuI and BglII and the 107 base pair fragment was isolated. These two DNA fragments were ligated into pDECΔ previously digested with BstEII and partially digested with BglII as described above.

Construction of pDEC(NO2)

pDEC(NO2) was assembled from pDEC(O62)(HCG-EPO) and pDEC(N47) ($Asn^{30}Thr^{32}Val^{87}Asn^{88}Thr^{90}$). pDEC(N47) was digested with StuI and BglII and the 610 bp DNA fragment containing the $Asn^{30}Thr^{32}Val^{87}Asn^{88}Thr^{90}$ mutations was isolated with GeneClean™. pDEC(O62) was digested with StuI and BglII and the 107 base pair fragment was isolated. These two DNA fragments were ligated into pDECΔ previously digested with BstEII and partially digested with BglII as described above.

Construction of pDEC(N16) ($Ser^{87}Asn^{88}Thr^{90}Ala^{162}$)

pDEC(N16) was assembled from pDEC(N14) ($Ser^{87}Asn^{88}Thr^{90}$) and pDEC258($Ala^{162}$). pDEC258 was constructed using procedures for in vitro mutagenesis described above and changing the AGG codon to GCG at position 162. pDEC(N14) was digested with StuI and BglII and the 610 bp DNA fragment containing the $Ser^{87}Asn^{88}Thr^{90}$ mutations was isolated with GeneClean™. pDEC258 was digested with StuI and BglII and a 210 base pair fragment was isolated. These two DNA fragments were ligated into pDECΔ previously digested with BstEII and partially digested with BglII as described above.

Construction of pDEC(R1), (R2) and (R3)

To remove glycosylation sites from pDEC(N14), m13-EPO(N14) containing ser87 asn88 and thr90 mutations was subjected to in vitro mutagenesis as described above using the following primers:

```
5' GGAGGCCGAGCAGATCACGACGG 3'   GLN24   SEQ ID NO:21
5' CTTGAATGAGCAGATCACTGTCC 3'   GLN38   SEQ ID NO:22
5' CTGTTGGTCCAGTCTTCCCAG 3'     GLN83   SEQ ID NO:23
```

The resulting plasmids were designated pDEC(R1) ($gln^{24}$ $ser^{87}$ $asn^{88}$ $thr^{90}$) pDEC(R2) ($gln^{38}$ $ser^{87}$ $asn^{88}$ $thr^{90}$) and pDEC(R3) ($gln^{83}$ $ser^{87}$ $asn^{88}$ $thr^{90}$). m13EC-1 was also

```
5' CCTGTAGGACAGGGGACAGATCCTCTTCCTCAAAGGCCCCTCCCCCAGCCTTC-
3' GGACATCCTGTCCCCTGTCTAGGAGAAGGAGTTTCCGGGGAGGGGGGTCGGAAG-
                                                                    SEQ ID NO:19
5' CAAGTCCATCCCGACTCCCGGGGCCCTCGGACACCCCGATCCTCCCACAATGA
                                                                    SEQ ID NO:20
3' GTTCAGGTAGGGCTGAGGGCCCCGGGAGCCTGTGGGGCTAGGAGGGTGTTACTCTAG
``` subjected to in vitro mutagenesis with the above oligonucleotide primers resulting in pEC10 (gln$^{24}$) and pEC8 (gln$^{38}$). pEC9 (gln$^{83}$) was constructed using the primer

```
5' CCTGTTGGTCCAGTCTTCCCAGC 3' GLN83 SEQ ID NO:24
``` cDNA clones of human erythropoietin and analogs corresponding to [Asn$^4$, Ser$^6$] EPO, [Asn$^9$, Ser$^{11}$] EPO, [Asn$^{69}$] EPO, [Asn$^{124}$] EPO, [Asn$^{125}$, Ser$^{127}$] EPO, [Asn$^{163}$, Ser$^{165}$] EPO, [Thr$^{125}$] EPO and [Pro$^{124}$, Thr$^{125}$] EPO and cDNA clones of analogs described in Tables 3,4 and 5, were transferred into COS-1 cells (ATCC No. CRL-1650) by electroporation. COS-1 cells were harvested from semiconfluent dishes, washed with medium (Dulbecco's modified essential medium containing 5% fetal calf serum and 1% L-glutamine/penicillin/streptomycin (Irvine Scientific)) and resuspended at 4×10$^6$ cells/ml. One ml of cells was transferred to an electroporation cuvette (Bio-Rad) and electroporated with a Bio-Rad Gene Pulser at 25 µFarads and 1600 volts in the presence of 100 to 200 µg of carrier DNA and 2 to 20 µg of plasmid DNA encoding the erythropoietin analog The electroporated cells were plated at 2×10$^6$ cells per 60 mm tissue culture dish in 5 ml of medium. Two to four hours after plating the medium was replaced with 5 ml of fresh medium. The conditioned medium was collected 3 to 5 days after electroporation.

EXAMPLE 7

Characterization of Erythropoietin Analogs

A. Determination of Carbohydrate Addition

A volume of supernatant containing 5–20 units from COS cells transfected with erythropoietin analog cDNAs as described in Example 6 was immunoprecipitated overnight at room temperature with a rabbit anti-erythropoietin polyclonal antibody. 20–80 µl of 1:1 Protein A-Sepharose in phosphate buffered saline (PBS) was added to the immunoprecipitate and allowed to incubate for one hour at room temperature. The samples were centrifuged, washed with PBS and, where indicated, the pellet was treated with N-glycanase to remove N-linked carbohydrate chains. The samples were analyzed by 15% SDS-polyacrylamide gel electrophoresis, transferred to nitrocellulose and subjected to Western analysis as described (Burnette et al. Anal. Biochem. 112, 195–203 (1981); Elliott et al. Gene 79, 167–180 (1989)) using a mixture of mouse anti-erythropoietin monoclonal antibodies. One such antibody, 9G8A, is described in Elliott et al. (1989) Blood 74, Supp. 1, A. 1228.

Figure 7:
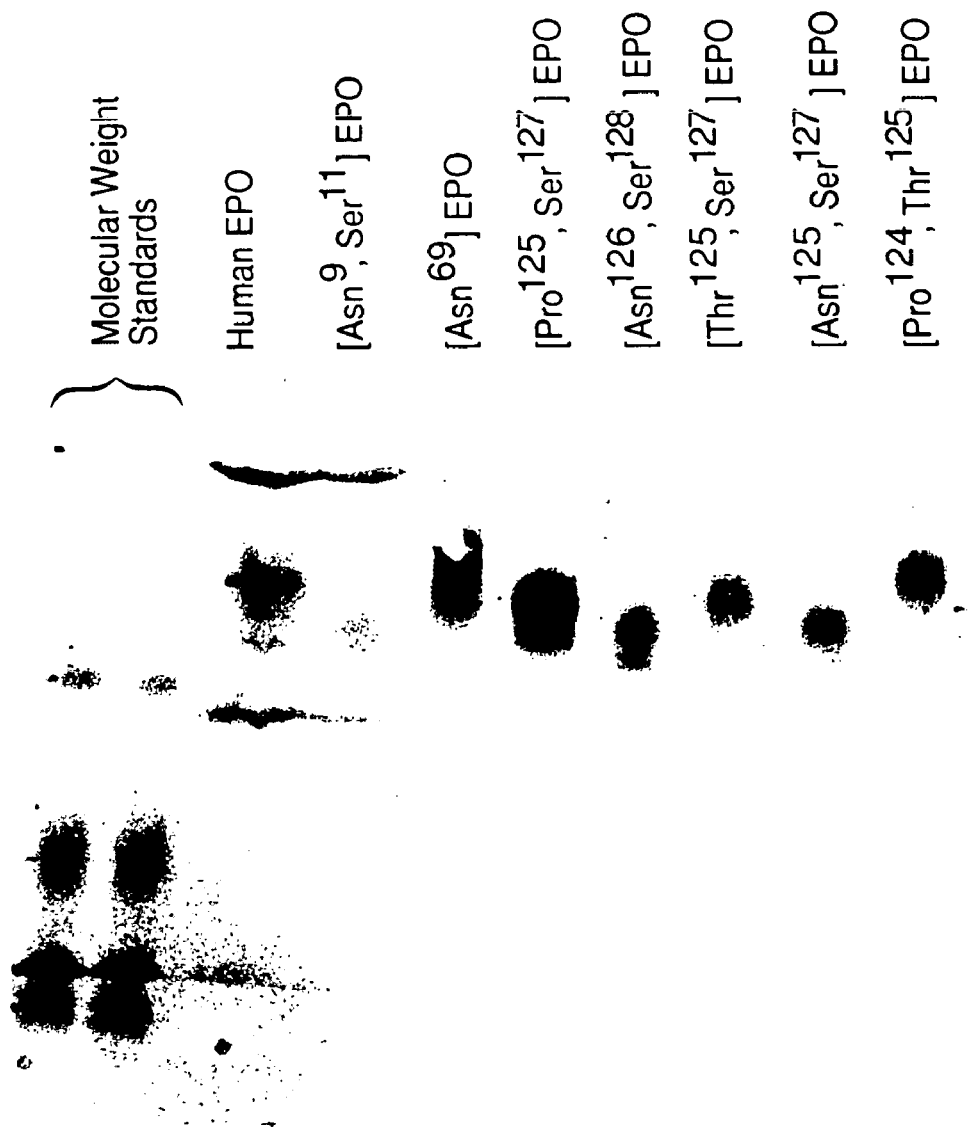
FIG. 7 shows a Western blot analysis of COS cell supernatants of human sequence erythropoietin and indicated erythropoietin analogs. The analogs [Asn$^9$, Ser$^{11}$] EPO, [Asn$^{69}$] EPO, [Asn$^{125}$, Ser$^{127}$] EPO, and [Pro$^{124}$, Thr$^{125}$] EPO are constructed as described in Example 6. Additional analogs [Pro$^{125}$, Thr$^{127}$] EPO and [Asn$^{126}$, Ser$^{128}$] EPO which do not contain additional carbohydrate chains are shown for comparison.
Figure 8:
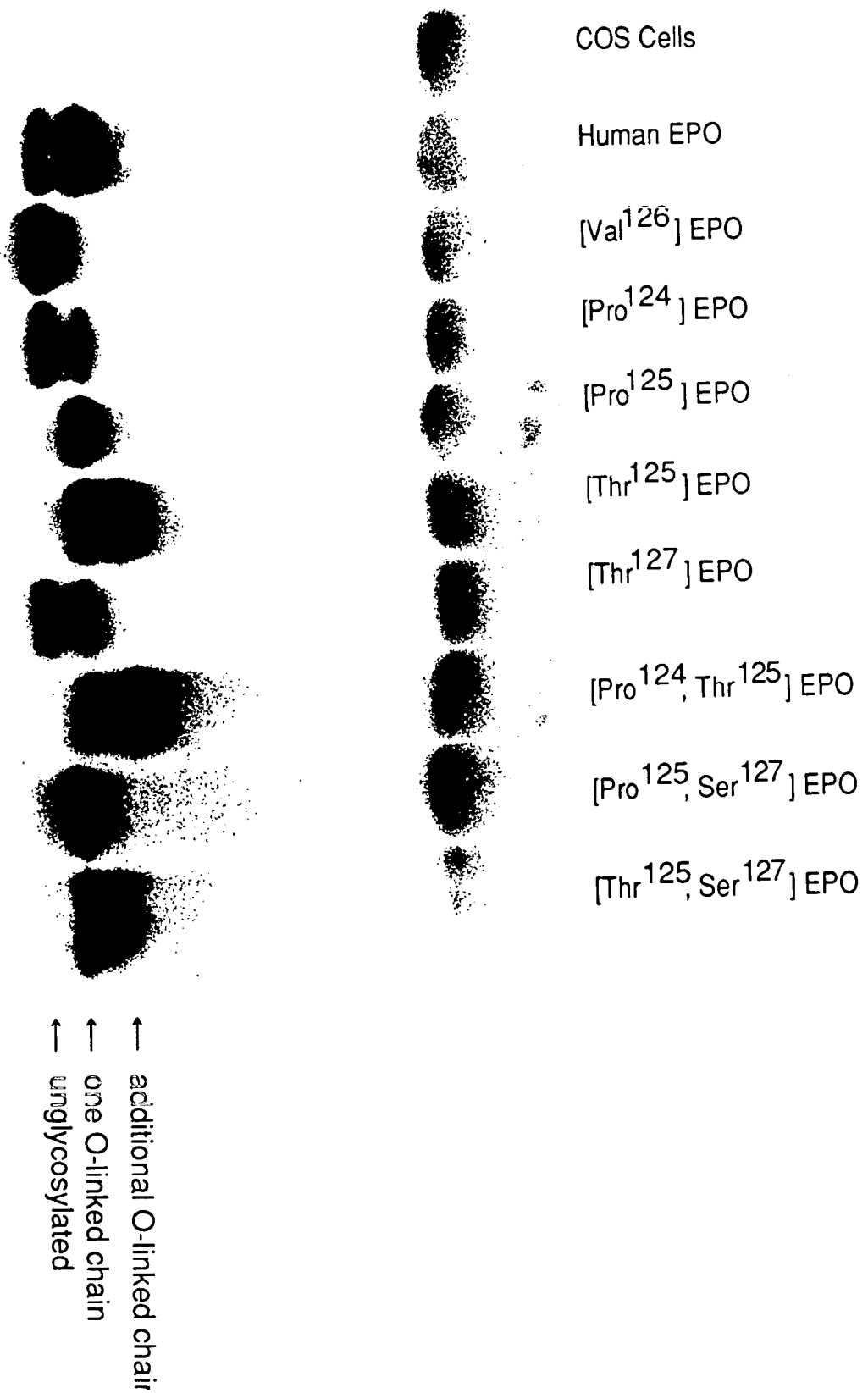
FIG. 8 shows a Western blot analysis of COS cell supernatants of human sequence erythropoietin and indicated erythropoietin analogs after treatment with N-glycanase. The analogs [Thr$^{125}$] EPO and [Pro$^{124}$, Thr$^{125}$] EPO were constructed as described in Example 6. The analogs [Val$^{126}$] EPO, [Pro$^{124}$] EPO, [Pro$^{125}$] EPO, [Thr$^{127}$] EPO, [Pro$^{125}$, Ser$^{127}$] EPO and [Thr$^{125}$, Ser$^{127}$] EPO are shown for comparison.
Figure 10:
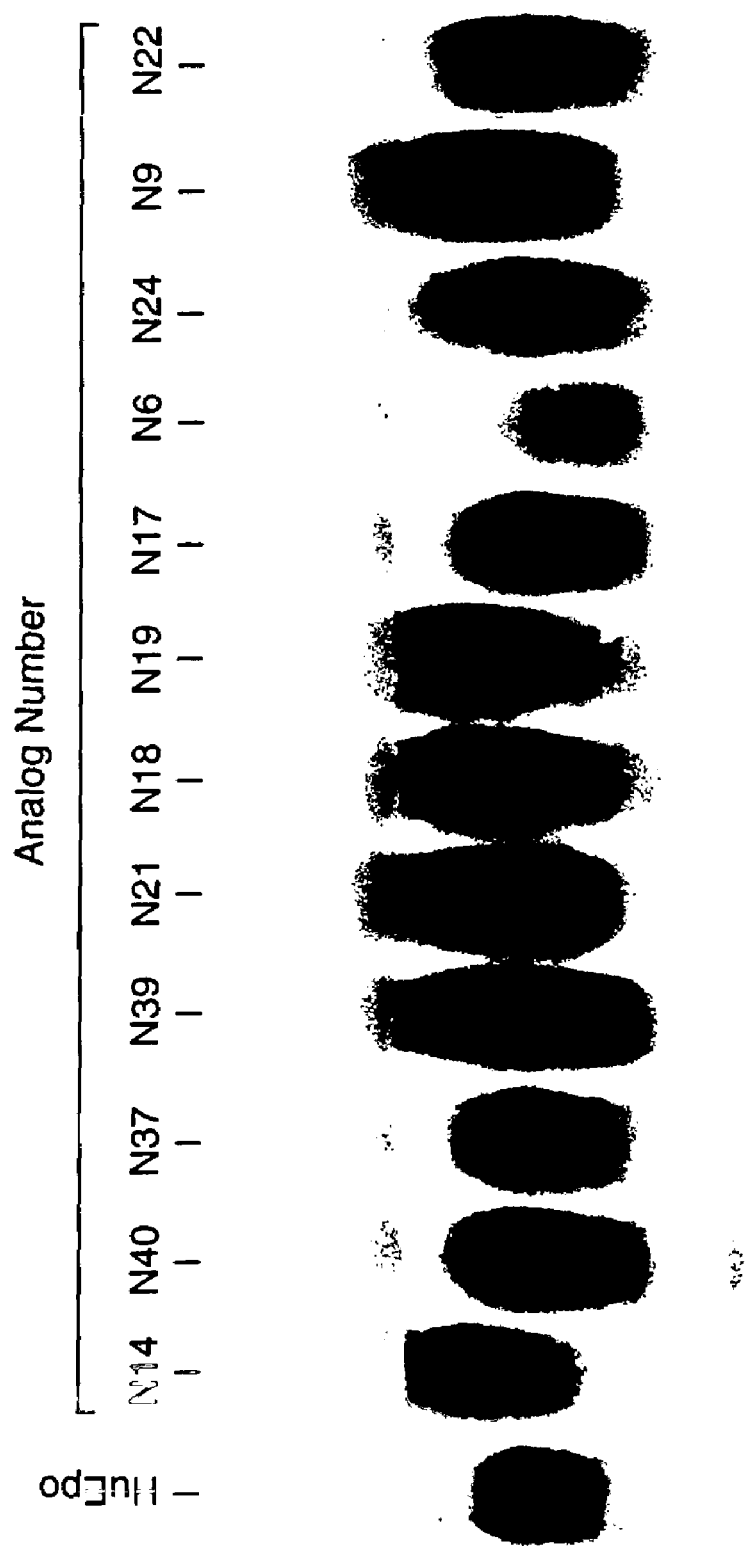
FIG. 10 shows a Western blot analysis of COS cell supernatants of recombinant human erythropoietin (rHuEPO) and selected analogs. The construction of the analogs is described in Example 6. Analogs N9, N14, N18, N19, N21, N24 and N39 have at least one additional carbohydrate chain as evidenced by slower gel mobility.

Analysis of COS cell supernatants transfected with [Asn$^{69}$] EPO and [Asn$^{125}$, Ser$^{127}$] EPO cDNA revealed increased protein size compared to human sequence erythropoietin. This increased size is indicative of an additional N-linked carbohydrate chain (FIG. 7). Treatment of supernatants from COS cells transfected with [Thr$^{125}$] EPO and [Pro$^{124}$, Thr$^{125}$] EPO cDNA with N-glycanase revealed an increased protein size compared to human sequence erythropoietin. This increased size is indicative of an additional O-linked carbohydrate chain (FIG. 8). Western blot analysis of other selected analogs is shown in FIG. 10.

Figure 11:
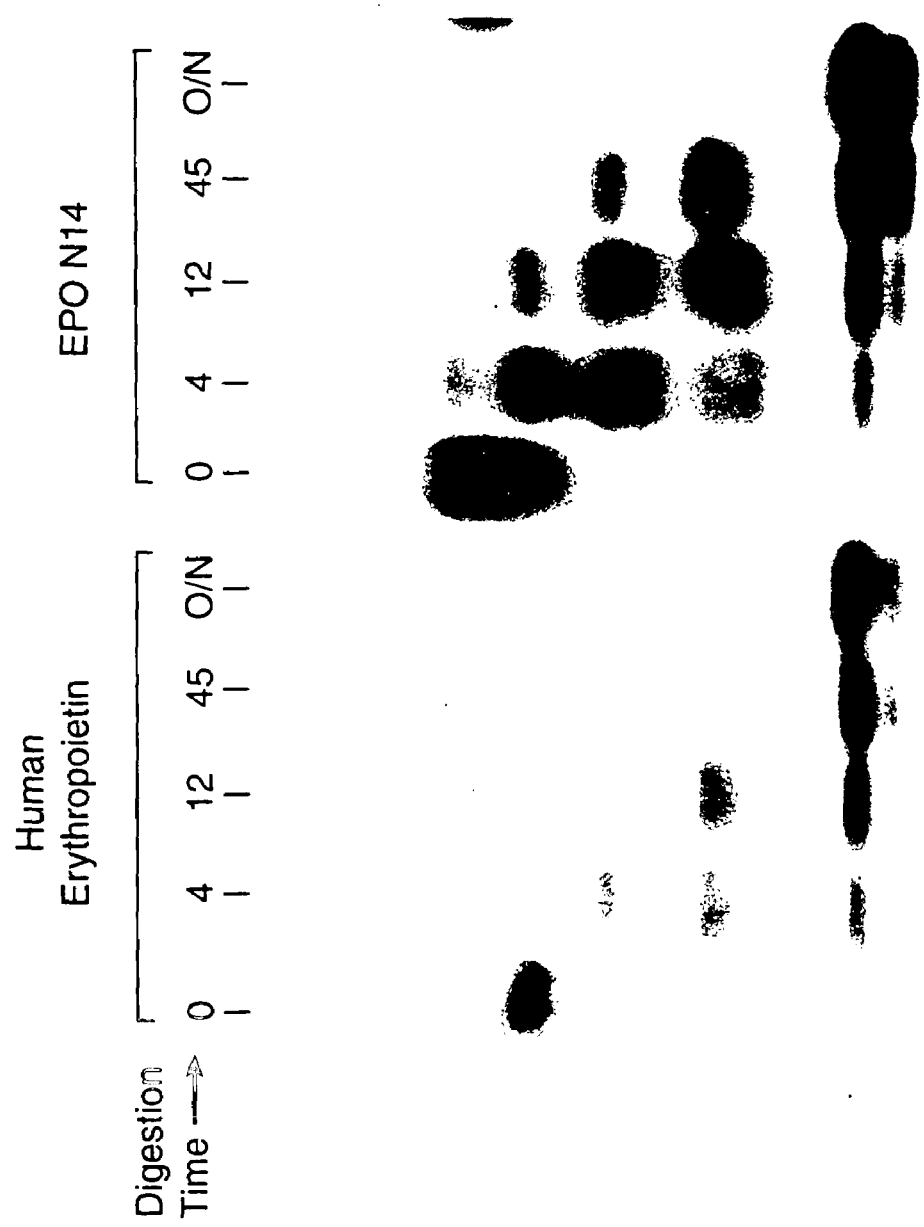
FIG. 11 shows a Western blot analysis of COS cell supernatants of recombinant human erythropoietin and EPO N14 analog during N-glycanase digestion. Time points were taken at 0, 4, 12 and 45 minutes and after overnight digestion.

To determine the number of N-linked carbohydrate chains attached to EPO, partial N-glycanase digestions were performed. Analogs or rHuEPO were expressed in CHO cells and conditioned serum free medium was collected. Tubes contained 40 units of EPO (volume adjusted to 15 µl with H$_2$O) To each tube was added 10 µl 0.5% SDS and each sample was boiled for 3 minutes. Then the following components were added, 10.8 µl 0.5M NaPO$_4$ pH8.6, 5 µl 7.5% nonidet P40 and 1.5 µl of 250 unit/ml N-glycanase (Genzyme). Samples were incubated for the indicated times at 37° C. The reaction was stopped by the addition of SDS-PAGE sample buffer (see above) and then subjected to SDS-PAGE western analysis (10% acrylamide) using an anti-EPO polyclonal antibody and a anti-rabbit Vectastain™ kit (Vector laboratories) with 4-chloronaphthol as substrate. An analysis of N-linked chains using this method is shown in FIG. 11 for human erythropoietin and analog N14.

B. Assays for Erythropoietin Analog Activity

RIAs were performed according to Egrie et al., supra. EIAs were performed with CLINIGEN™ EIA kit (R and D Systems) using procedures supplied by the manufacturer. The in vivo biological activity of erythropoietin analogs was determined on supernatants from CHO cells expressing an erythropoietin analog or on purified erythropoietin obtained from CHO cell conditioned medium as described below using the exhypoxic polycythemic mouse bioassay (Cotes et al., supra).

In vitro erythropoietin activity was determined by the erythroid colony forming assay as described by Iscove et al. J. Cell Physiol. 83, 309–320 (1974) with modifications. The mononucleated cells from human bone marrow cells were partially purified on a ficoll-paque cushion and washed in Iscove medium before plating to remove the adherent cells. The culture medium contained 0.9% methyl cellulose and did not include any bovine serum albumin. The erythroid colonies were scored after 8 to 10 days of culture.

The erythropoietin analogs transfected and expressed in COS cells as described in Example 6 were analyzed in crude COS cell supernatants using RIA, EIA and an erythroid colony forming assay. Purified human sequence erythropoietin has an in vitro activity that was comparable to the RIA activity as determined by the above-mentioned assays. The analogs [Asn$^{69}$] EPO, (Thr$^{125}$) EPO and [Pro$^{124}$, Thr$^{125}$] EPO exhibited an in vitro activity that was comparable to the RIA activity and gave evidence of having additional carbohydrate chains (as determined in Section A). [Thr$^{125}$] EPO and analogs N4, N11, N14, N16, N18, N47, N48, O62, NO1 and NO2 were analyzed further by transfecting a cDNA clone encoding the erythropoietin analog into CHO cells, and subjecting the CHO cell supernatants to RIA or EIA and in vivo biological assays. The results are shown in Table 6. In vivo activities for analogs R1, R2 and R3 expressed in CHO cell supernatants are shown in Table 7.

TABLE 6

ERYTHROPOIETIN ANALOGS HAVING
ADDITIONAL CARBOHYDRATE CHAINS

| EPO Sequence | N-Linked$^a$ Chains | O-Linked Chains | In Vivo$^b$ Activity RIA or EIA |
|---|---|---|---|
| Human | 3$^c$ | 1$^d$ | 0.6 |
| Asn$^{30}$Thr$^{32}$ | 3 to 4$^c$ | n.t. | 1.1 |
| Asn$^{51}$Thr$^{53}$ | 4 | n.t. | n.t. |
| Asn$^{57}$Thr$^{59}$ | 4 | n.t. | n.t. |
| Asn$^{69}$ | 4 | reduced$^e$ | n.t. |
| Asn$^{69}$Thr$^{71}$ | 4 | n.t. | 0.25–0.7 |
| Ser$^{68}$Asn$^{69}$Thr$^{71}$ | 4 | n.t. | n.t. |
| Val$^{87}$Asn$^{88}$Thr$^{90}$ | 4$^c$ | n.t. | 1.8 |
| Ser$^{87}$Asn$^{88}$Thr$^{90}$ | 3 to 4$^c$ | normal | 1.0 |
| Ser$^{87}$Asn$^{88}$Gly$^{89}$Thr$^{90}$ | 4 | n.t. | n.t. |
| Ser$^{87}$Asn$^{88}$Thr$^{90}$Thr$^{92}$ | 4 | reduced$^e$ | n.t. |
| Asn$^{89}$Ile$^{90}$Thr$^{91}$ | 4 | n.t. | n.t. |

TABLE 6-continued

ERYTHROPOIETIN ANALOGS HAVING ADDITIONAL CARBOHYDRATE CHAINS

| EPO Sequence | N-Linked[a] Chains | O-Linked Chains | In Vivo[b] Activity RIA or EIA |
|---|---|---|---|
| Ser[87]Asn[89]Ile[90]Thr[91] | 4 | n.t. | n.t. |
| Ser[87]Asn[88]Thr[90]Ala[162] | 4 | n.t. | 1.8 |
| Asn[136]Thr[138] | 3 to 4 | n.t. | n.t. |
| Asn[138]Thr[140] | 3 to 4 | n.t. | n.t. |
| Asn[69]Thr[71]Ser[87]Asn[88]Thr[90] | 4 to 5 | n.t. | 0.025–0.25 |
| Asn[30]Thr[32]Val[87]Asn[88]Thr[90] | 4 to 5[c] | normal | 1.8 |
| Thr[123] | 3 | 1 and 2[f] | n.t. |
| Thr[125] | 3 | 1 and 2[f] | 0.7 |
| Pro[124]Thr[125] | 3 | 1 and 2[f] | n.t. |
| HCG C-terminal extension | 3 | at least 3[g] | 1.0–1.3 |
| Ser[87]Asn[88]Thr[90] HCG extension | 4 | at least 3[g] | 1.5 |
| Asn[30]Thr[32]Val[87]Asn[88]Thr[90] HCG extension | 4 to 5 | at least 3[g] | 0.8 |

TABLE 6 FOOTNOTES
[a]The number of additional N-linked chains was estimated based upon the mobility of the analog polypeptides in SDS gels as described in Example 7A.
[b]Ratio of in vivo activity of analog to amount of erythropoietin analog. Activity measurements were done on CHO cell supernatants of analogs using the mouse polycythemic bioassay. Quantities of erythropoietin analogs in CHO cell supernatants were determined by RIA or EIA as described in the text.
[c]Confirmation of the number of additional carbohydrate chains was made by examining the glycoprotein migration in SDS-gels after partial N-glycanase digestion as described in Example 7A.
[d]O-linked chain at Ser[126] is present on 70% of human erythropoietin molecules.
[e]Analogs having reduced O-glycosylation have a carbohydrate chain at Ser[126] on less than 70% of the molecules.
[f]Thr[123] EPO has two O-linked chains on greater than 60% of the molecules. Thr[125] EPO has two O-linked chains on about 40% of the molecules. Pro[124]Thr[125] EPO has two O-linked chains on greater than 80% of the molecules.
[g]These analogs have at least three O-linked chains and may have four or five. HCG alone is known to have four O-linked chains.
n.t. not tested

TABLE 7

ACTIVITY OF HUMAN ERYTHROPOIETIN AND ANALOGS HAVING CARBOHYDRATE SITE REARRANGEMENTS

| EPO Sequence | N-Linked Chains | In vivo Activity RIA or EIA |
|---|---|---|
| Human | 3 | 0.69 |
| Gln[24] | 2 | 0.16 |
| Gln[38] | 2 | 0.16 |
| Gln[83] | 2 | 0.23 |
| Gln[24]Ser[87]Asn[88]Thr[90] (R1) | 3 | 0.69 |
| Gln[38]Ser[87]Asn[88]Thr[90] (R2) | 3 | 0.41 |
| Gln[83]Ser[87]Asn[88]Thr[90] (R3) | 3 | 0.50 |
| Ser[87]Asn[88]Thr[90] | 3 to 4 | 1.48 |

Ratio of in vivo activity to RIA or EIA was determined as described in footnote a of Table 6.

C. Preparation of Isoform Mixtures Derived from Erythropoietin Analogs

[Thr[125]] EPO (EPO O50)

The erythropoietin analog [Thr[125]] EPO was constructed as described in [Section A] Example 6. An 810 bp. erythropoietin cDNA fragment carrying the [Thr[125]] mutation was isolated by cleaving the plasmid pEC containing the [Thr[125]] mutation with BstEII and BglII and ligating the fragment to pDECΔ, [a derivative of pDSα2] (described in Example 6).

Figure 9:
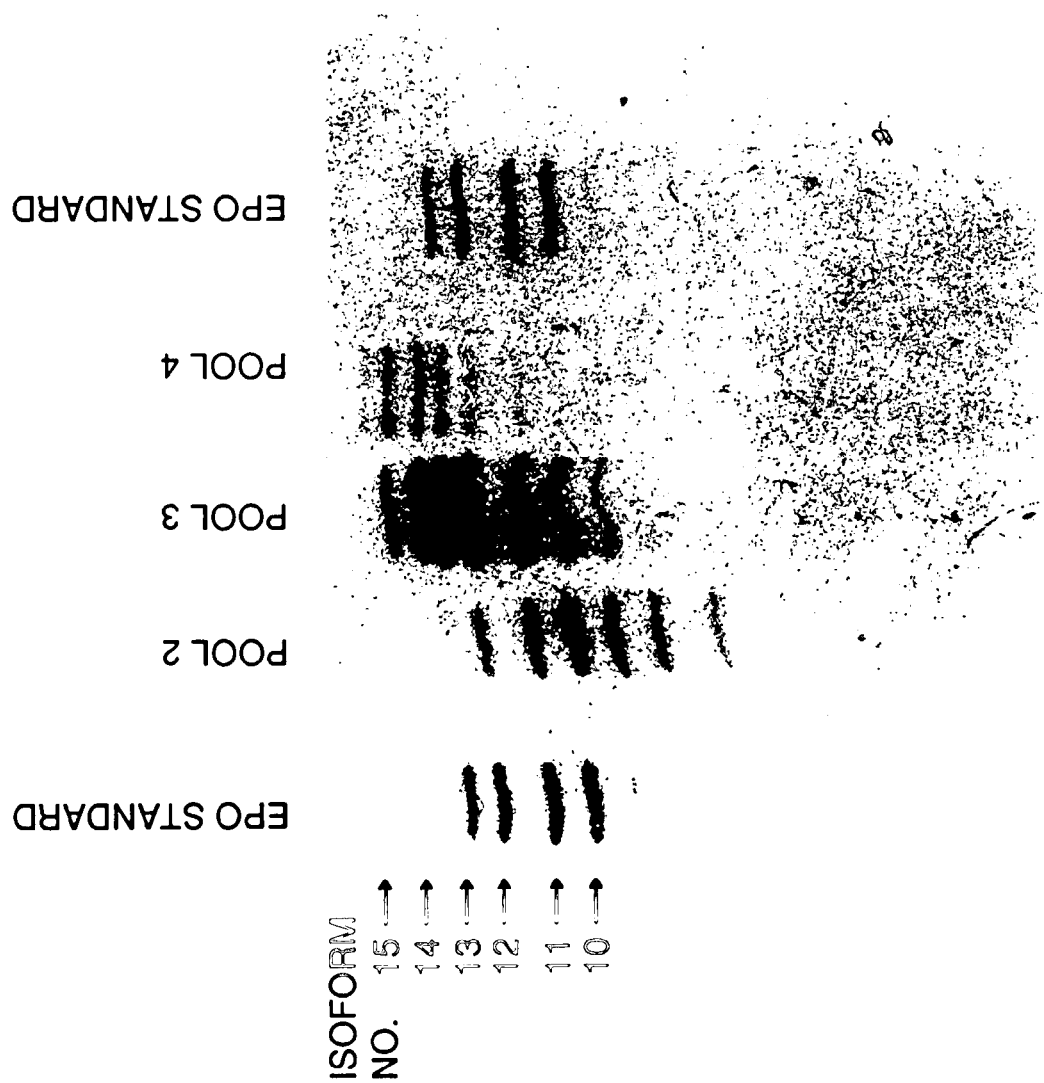
FIG. 9 shows an isoelectric focusing gel of pools 2, 3 and 4 obtained by Q-Sepharose and C4 reverse phase chromatography of cell medium that supported the growth of CHO cells transfected with erythropoietin cDNA containing the [Thr$^{125}$] mutation. Purified recombinant erythropoietin containing a mixture of isoforms were obtained using procedures described in Example 2 of Lai et al., supra, except that DEAE-Agarose chromatography is replaced by Q-Sepharose chromatography, is also shown in the left and right lanes of the gel.

Plasmid pDECΔ containing [Thr[125]] erythropoietin cDNA was transfected into DHFR-deficient CHO cells. 770 ml of CHO cell conditioned medium was concentrated using a 10,000 dalton molecular weight cut-off membrane and diafiltered against 10 mM Tris-HCl, pH 8.6 to a final volume of 34 ml. A 17 ml. aliquot of the concentrate was loaded onto a Q-Sepharose fast flow column (5 ml bed volume) equilibrated in the same buffer and eluted in a linear gradient of 0–250 mM NaCl in 10 mM Tris-HCl, pH 8.6. Aliquots of column fractions, either untreated or digested with N-glycanase, were analyzed by SDS-PAGE or IEF and pools (designated 2, 3 and 4) were made based upon the isoform and/or carbohydrate composition of the fractions. Each pool was loaded onto a Vydac C4 column (214TPB 2030; 1 cm diameter; 1.8–2.5 ml bed volume; 0.34 ml/min) and washed with two column volumes of 20% ethanol in 10 mM Tris-HCl, pH 7.0. The columns were eluted with linear gradients of 20–94% ethanol, 10 mM Tris, pH 7.0. Pools were made, diluted into 10 mM Tris-HCl, pH 7.0, and loaded onto Q-Sepharose fast flow columns. Following a wash in 10 mM Tris-HCl, pH 7.0, the samples were eluted with 20 mM sodium citrate, 250 mM NaCl, pH 7.0. The purified [Thr[125]] pools were analyzed by IEF and are shown in FIG. 9. These pools were also analyzed for in vivo biological activity as described above (Cotes et al., supra) and the results shown in Table 8.

Ser[87]Asn[88]Thr[90] EPO (EPO N14)

Prep. 1

The EPO N14 analog was purified using a three step procedure consisting of ion exchange chromatography, reverse phase chromatography and gel filtration chromatography. During the ion exchange step, fractions were pooled to give a mixture of isoforms having high levels of sialic acid. Two additional pools were made during reverse phase chromatography containing the analog with or without aggregate. The details of the purification are set out below.

1. Conditional medium from CHO cells expressing the EPO N14 analog was harvested and concentrated approximately 2.5-fold using a stirred cell with YM10 membrane (Amicon) and diafiltered against 10 mM Tris pH 8.5.

2. The concentrated medium was loaded at ~12 $A_{280}$/ml resin to Q-Sepharose FF (Pharmacia) column equilibrated in 10 mM Tris pH 8.5 at a flow rate of 0.2 cm/min.

3. Following the load, the column was washed with 3 column volumes (CV) of 10 mM Tris pH 8.5 and eluted with a gradient of 0–0.5M NaCl/10 mM Tris pH 8.5 in 50CV. 1CV fractions were collected.

4. A sample of each fraction was run on an IEF gel pH 3–5. Based on the isoform distribution on IEF, a fraction pool containing largely isoforms 11–18 was made. EDTA was added to the pool to 1 mM final concentration.

5. The isoform pool was loaded at ~5 $A_{280}$/ml resin to a reverse phase C4 column (Vydac) equilibrated in 20% ethanol/10 mM Tris pH 7.0 at a flow rate of 2.5 cm/min. The column was washed with 1CV of 20% ethanol/10 mM Tris pH 7.0 and eluted with a gradient of 20–94% ethanol/10 mM Tris pH 7.0 in 30CV at a flow rate of 1 cm/min. 0.2CV fractions were collected.

6. A sample of each fraction was analyzed by non-reducing 12% SDS-PAGE. Two separate pools were made based on the presence of aggregate observed on SDS gels. Pool #1 contained EPO analog but no aggregate. Pool #2 contained both EPO analog and aggregate.

7. Pool #1 was concentrated approximately 65-fold and pool #2 approximately 250-fold using Centricon 10's (Amicon). Each pool was buffer exchanged into 20 mM NaCitrate/100 mM NaCl pH7.0.

8. Each pool was individually purified on HPLC BioSil SEC-250 (BioRad) column equilibrated in 20 mM NaCitrate/100 mM NaCl pH7.0. Pools were loaded at <6 A280/ml resin at a flow rate of 2.26 cm/min. Peaks corresponding to monomeric analogs were collected from each run.

9. The absorbance of each pool was measured and a portion of each pool was concentrated for analysis by SDS-PAGE and IEF gels. Pool #1 had a distribution of isoforms 15–17 and was used for pharmacokinetic and receptor binding studies.

Prep. 2

EPO N14 analog was purified using a three step procedure consisting of ion exchange chromatography, reverse phase HPLC, and hydroxylapatite chromatography. During the ion exchange step, the analog was divided into three pools containing different mixtures of isoforms. The details of the purification are set out below.

1. Supernatant from CHO cells expressing EPO N14 were harvested and concentrated approximately 10-fold using a Filtron Mini-Ultrasette tangential flow device and diafiltered against 10 mM Tris pH 8.5.

2. The concentrated medium was loaded at ~10 A280/ml resin to Q-Sepharose FF (Pharmacia) column equilibrated in 10 mM Tris pH 8.5 at a flow rate of 0.2 cm/min.

3. Following the load, the column was washed with three column volumes (CV) of 10 mM Tris pH8.5 and eluted with a gradient of 0–0.5M NaCl/10 mM Tris pH 8.5 in 50CV. 1 CV fractions were collected.

4. A sample of each fraction was run on an IEF gel pH 3–5. Three separate fraction pools were prepared based on the isoform distribution as determined by IEF. A low isoform pool (isoform 4–12), a medium isoform pool (isoform 5–15), and a high isoform pool (isoform 6–18) were made.

5. Each isoform pool was individually purified on a Vydac C4 reverse phase HPLC column. The column was developed with a gradient from 0.1% TFA/$H_2O$ to 0.1% TFA/75% acetonitrile at a rate of 1% increase in acetonitrile per minute.

6. The analog peak from each pool was collected and diluted with 4 volumes 80 mM Tris HC1/20 mM Tris base, then concentrated and buffer exchanged into 10 mM Tris pH 7.2 using solvent resistant Centricon 3's.

7. Each sample was diluted to 2 $A_{280}$/ml in 10 mM Tris pH 7.2 and an equal volume of 4M Guanidine HCl (GuHC1), 10 mM CHAPS, 10 mM Tris pH 7.2 was added for a final sample concentration of 1 $A_{280}$/ml. Each sample was loaded onto a hydroxylapatite minicolumn equilibrated with 2M GuHC1, 5 mM CHAPS, 10 mM Tris pH 7.2. The column was washed with equilibration buffer and 1 CV fractions of flow through were collected.

8. The absorbance of fractions was measured and pools were made and buffer exchanged into 10 mM Tris pH 7.2 using Centricon 10's. The absorbance of each pool was measured.

Figure 12:
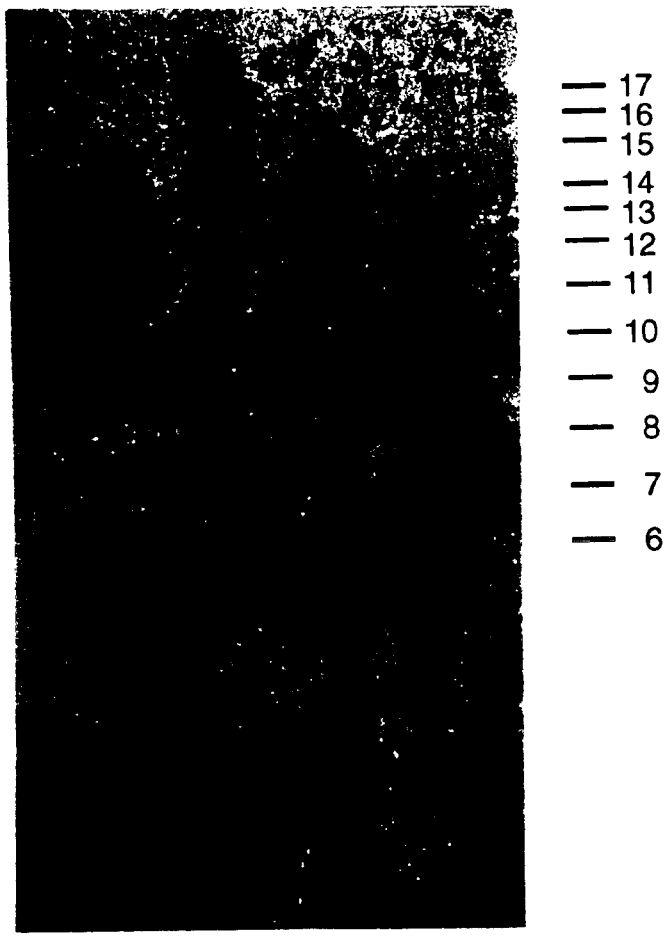
FIG. 12 shows an isoelectric focusing gel of EPO N14 analog isoform preparations. The low isoform pool contains EPO N14 analog having mostly 6–12 sialic acids per molecule, the medium isoform pool contains analog N14 having mostly 10–15 sialic acids per molecule, and the high isoform pool contains EPO N14 analog having mostly 12–17 sialic acids per molecule.

The final pools were analyzed by SDS-PAGE and IEF gels. The IEF gels are shown in FIG. 12. The RIA and in vivo activity assays were performed as described in Example 7A. The in vivo activity of the final isoform pools is reported in Table 8. The high sialic acid isoform pool was used in experiments to determine the increase in the hematocrit of mice.

TABLE 8

ACTIVITY OF ISOFORMS FROM ERYTHROPOIETIN ANALOGS

| EPO Sequence | Isoform Pool | In vivo activity u/mg. peptide[a] |
|---|---|---|
| $Thr^{125}$ | Isoforms 8–12 | 147,000[b] |
| | Isoforms 9–15 | 215,000[b] |
| | Isoforms 13–15 | 111,000[b] |
| $Ser^{87}Asn^{88}Thr^{90}$ | Isoforms 7–12 | 132,000 ± 17,000 |
| | Isoforms 10–14 | 233,000 ± 39,000 |
| | Isoforms 12–17 | 272,000 ± 14,000 |

[a]milligrams of erythropoietin peptide were calculated from $A_{280}$ of the $Ser^{87}Asn^{88}Thr^{90}$ EPO isoform pools using an extinction coefficient of 0.93 for a 1 mg/ml solution.
[b]Standard deviations for $Thr^{125}$ EPO isoform pools are not reported since activity assays were done either once or twice.

EXAMPLE 8

Biological Properties of EPO N14 Analog

The activities of isoform pools of EPO N14 analog, recombinant human erythropoietin (rHuEPO) and isolated rHuEPO isoform 14 were compared in i.v. pharmacokinetic assays, receptor binding assays and hematocrit studies. EPO N14 isoform pools were prepared as described in Example 7C. rHuEPO was prepared according to Lai et al. supra. rHuEPO isoform 14 was purified as follows: rHuEPO consisting of a mixture of isoforms 10, 11, 12, 13, 14 and 15 was loaded to a Q-Sepharose Fast Flow column (Dimensions=2.2 cm dia.×3.4 cm ht.) equilibrated in 10 mM Tris pH 7.2. The loaded column was equilibrated to 2 mM acetic acid/6 M urea ("A" buffer) then a multiphasic gradient designed to optimize purification of isoforms 13 and 14 was run. The gradient was 0% to 7.3% 800 mM acetic acid/6 M urea ("B" buffer) in 750 mL, 7.3% to 11.4% "B" buffer in 750 mL, 11.4% to 26.8% "B" buffer in 1250 mL, 26.8% to 62.4% "B" buffer in 1250 mL, then 62.4% to 100% "B" buffer in 700 mL. Fractions of 12.5 mL were collected, neutralized with ammonium hydroxide, then assayed by isoelectric focusing in polyacrylamide gels. Those fractions containing pure isoform 14 were pooled together, concentrated with an Amicon stirred cell equipped with a YM-10 membrane then buffer exchange to water.

A. IV Pharmacokinetics

Two separate studies were performed to compare the pharmacokinetic parameters of EPO N14 analog (isoforms 15–17) and isolated isoform 14 to rHuEPO.

In each study 1 µCi of either $^{125}$I-isolated isoform 14, $^{125}$I-EPO N14 analog, or $^{125}$I-recombinant human erythropoietin (Amersham) was injected intravenously into a carotid cannula in male Sprague-Dawley rats weighing between 310–378 g. At various time points after administration, 0.3 ml of blood was collected and serum was prepared by centrifugation. The $^{125}$I-EPO (either recombinant human, isolated isoform 14, or EPO N14 analog) concentration in 0.1 ml of each serum sample was then determined following an overnight 4° C. incubation with 90% ethanol. The ethanol-precipitated $^{125}$I-EPO in each serum sample was counted in a gamma counter and the resulting pharmacokinetic curves are shown in FIG. 13. The pharmacokinetic parameters were determined for each rat using PCNONLIN 4.0 nonlinear regression analysis (Statistical Consultants, 1992) and the results for each group were averaged. The results from the EPO N14 analog and the isolated isoform 14 pharmacokinetic studies are summarized in Table 9.

As seen in Table 9, there is a significant difference in the serum clearance of EPO N14 analog when compared to that calculated for recombinant human erythropoietin. The recombinant human erythropoietin displayed the fastest beta half-life of 3.10 hrs compared to 3.97 hrs for isolated isoform 14 and 4.36 hrs for EPO N14 analog. The recombinant human erythropoietin group also had the fastest clearance half-life of 1.78 hrs compared to 2.40 hrs for isolated isoform 14 and 3.03 hrs for EPO N14 analog.

reduce $^{125}$I-rHuEPO binding to OCIM1 cells by 50%. In the same three assays, unlabeled rHuEPO required an average of 0.51±0.15 ng to compete with the binding of 0.5 ng of $^{125}$I-rHuEPO. Based upon these results, a 5.25 fold excess of EPO N14 was required to compete the binding of $^{125}$I-rHuEPO to the EPO receptor compared to unlabeled r-HuEPO (p<0.01).

An additional experiment was performed to make a direct comparison between EPO N14 analog, isolated isoform 14, and recombinant erythropoietin for binding to the erythropoietin receptor. The results of this experiment indicate that

TABLE 9

SUMMARY OF THE PHARMACOKINETIC PARAMETERS OF rHuEPO, rHuEPO ISOFORM 14 AND EPO N14 (ISOFORMS 15–17) FOLLOWING I.V. ADMINISTRATION

| Preparation | | HalfLife (Hours) Alpha | Beta | AUC (cpm-hr/ml) 0–∞ Hr. | VD (mL/Kg) | Elimination Rate Constant (Hr$^1$) | Clearance (ml/Kg-hr) | Clearance Half-Life (Hours) |
|---|---|---|---|---|---|---|---|---|
| rHuEPO | Mean | 0.332 | 3.10 | 308901 | 44.9 | 0.400 | 6.14 | 1.78 |
| *n = 6 | S.D. | 0.155 | 0.54 | 69187 | 8.3 | 0.069 | 1.36 | 0.27 |
| Isoform 14 | Mean | 0.388 | 3.97 | 483329 | 36.5 | 0.288 | 3.80 | 2.40 |
| n = 4 | S.D. | 0.066 | 0.40 | 53638 | 2.2 | 0.020 | 0.12 | 0.15 |
| EPO N14 | Mean | 0.422 | 4.36 | 692231 | 37.4 | 0.230 | 2.67 | 3.03 |
| n = 4 | S.D. | 0.165 | 0.36 | 40355 | 1.9 | 0.021 | 0.17 | 0.27 |

*The average of the recombinant human erythropoietin groups from the EPO N14 pharmacokinetic study (n = 4 for the recombinant human erythropoietin group) and from the isolated isoform 14 pharmacokinetic study (n = 2 for the recombinant human erythropoietin group).

B. Receptor Binding Assays

The interaction of EPO N14 analog (isoforms 15–17) with the erythropoietin receptor was studied by a cold displacement assay using human erythroleukemia OCIM1 cells (Papayannopoulou et al. Blood 64 (supp.1), 116a (1984)). Increasing concentrations of unlabeled EPO N14 were incubated with OCIM1 cells along with a constant concentration of $^{125}$I-rHuEPO to determine the amount of EPO N14 required to compete with $^{125}$I rHuEPO for binding to the receptor. As a comparison, increasing concentrations of unlabeled rHuEPO were also competed with a constant concentration of $^{125}$I-rHuEPO.

Unlabeled EPO N14 was diluted in assay buffer and added in amounts of 0.03 ng, 0.1 ng, 0.3 ng, 1.0 ng, 3.0 ng, 10.0 ng, and 30.0 ng (based on peptide mass). 0.5 ng of $^{125}$I-recombinant human EPO were added to all assay tubes followed by the addition of approximately 0.5×10$^6$ OCIM1 cells. The assay tubes were then incubated at 37° C. in a shaking water bath for 2 hours. Following the incubation, the solutions were centrifuged through a dibutyl phthalate/bi-phthalate oil solution to separate unbound $^{125}$I-rHuEPO from $^{125}$I-rHuEPO bound to OCIM1 cells. Cell pellets were isolated and the amount of $^{125}$I-rHuEPO bound to the cells was determined by gamma counting. Counts specifically bound to the cells were calculated and the concentration of unlabeled protein required to compete 50% of the $^{125}$I-rHuEPO binding in the absence of competitor was determined by linear regression analysis.

The results of three assays indicated that an average of 2.67±0.73 ng of unlabeled EPO N14 peptide was required to EPO N14 analog had a lower affinity for the receptor than isolated isoform 14. An approximate two-fold excess of EPO N14 analog was required to compete the binding of $^{125}$I-rHuEPO to the receptor compared to unlabeled isoform 14 (FIG. 14).

C. Hematocrit Study

An in vivo study was performed to compare the ability of EPO N14 high and low isoform pools (from prep 2 described in Example 7C), isolated isoform 14, and recombinant human EPO to increase the hematocrit of treated mice. The isoform distribution of EPO N14 high and low isoform pools used in this study is shown in FIG. 12.

CD1 mice (about 30 g) were injected intraperitoneally three times per week for a total of six weeks with one of the above preparations prepared in 0.25% mouse serum albumin, or with placebo (PBS with 0.25% mouse serum albumin). The dosage of erythropoietin preparations was based on peptide mass, so that a 30 g mouse received either 0.071 µg of peptide/dose for EPO N14 high pool, EPO N14 low pool, isoform 14, and r-HuEPO standard. An additional dosage group of 0.036 µg of peptide/dose was included for EPO N14 high pool and isoform 14. The hematocrits of all mice were determined at baseline and twice weekly thereafter by retroorbital bleeds. At the conclusion of the experiment, serum from all animals was collected and assayed for antibodies to the injected product. Data from animals judged to be negative for neutralizing antibodies was used for subsequent analysis.

As shown in FIG. 15, animals treated with the EPO N14 high isoform pool attained the highest group average hematocrits compared to the other preparations. Isoform 14, recombinant human EPO and the EPO N14 low isoform pool increased hematocrit to a lesser extent.

In order to compare the different erythropoietin preparations in a more quantitative manner, the average initial rate of hematocrit rise (0–11 days), area under the curve (0–39 days), and the total hematocrit increase were calculated (Table 10). By any of these criteria, the EPO N14 high isoform pool appears to be more active on a peptide mass basis than any other preparation tested. Both the EPO N14 high isoform pool and isoform 14 were more active than recombinant human EPO. The EPO N14 low pool had the lowest activity when any of the analyses was used for comparison.

TABLE 10

EFFECT OF EPO N14 (HIGH AND LOW ISOFORM POOLS), ISOFORM 14 AND rHuEPO ON THE HEMATOCRIT OF MICE

| Preparation | Dose (μg) | Rate of Hct Rise[1] (points/day) | Area Under Curve[2] | Total Hct Increase[3] (Hct points) |
|---|---|---|---|---|
| N14 High Pool | 0.071 | 1.46 | 619 | 25.4 |
| Isoform 14 | 0.071 | 1.19 | 546 | 22.6 |
| N14 High Pool | 0.036 | 0.98 | 428 | 19.1 |
| Isoform 14 | 0.036 | 0.76 | 284 | 10.7 |
| r-HuEPO | 0.071 | 1.0 | 424 | 17.5 |
| N14 Low Pool | 0.071 | 0.5 | 212 | 9.3 |

[1] Initial rate of hematocrit rise was calculated from days 0–11 by linear regression.
[2] Area under the curve was calculated from day 0–39 by trapezoidal summation.
[3] Total hematocrit increase was calculated as the group average hematocrit on day 39 minus group average hematocrit at baseline.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. An analog of human erythropoietin having the in vivo biological activity of increasing hematocrit comprising an amino acid sequence which differs from the amino acid sequence of human erythropoietin from residues 1–165 as shown in SEQ ID NO:26 at least by having one or more additional glycosylation site(s) and wherein a carbohydrate chain is attached to the additional site(s).

2. An analog of human erythropoietin comprising the amino acid sequence of human erythropoietin from residues 1–165 as shown in SEQ ID NO:26 except for one or more amino acid changes which provide for one or more additional glycosylation site(s) as compared to human erythropoietin, and the analog has more than four carbohydrate chains.

3. The analog of claims 1 or 2 wherein one additional glycosylation site is an N-linked glycosylation site having an N-linked carbohydrate chain attached thereto.

4. The analog of claims 1 or 2 wherein one additional glycosylation site is an O-linked glycosylation site having an O-linked carbohydrate chain attached thereto.

5. The analog of claims 1 or 2 which is the product of expression of an exogenous DNA sequence.

6. A DNA sequence encoding an analog of human erythropoietin according to any of claims 1 or 2.

7. A eucaryotic host cell transfected with a DNA sequence according to claim 6 in a manner allowing the host cell to express an analog of human erythropoietin.

8. A composition comprising an erythropoietin analog according to any of claims 1 or 2 together with a pharmaceutically acceptable diluent, adjuvant or carrier.

9. A method of increasing hematocrit in a patient in need thereof comprising administering a therapeutically effective amount of the composition of claim 8.

10. An analog of human erythropoietin comprising the amino acid sequence of human erythropoietin from residues 1–165 as shown in SEQ ID NO:26 except for one or more amino acid changes which provide for one or more additional glycosylation site(s) as compared to human erythropoietin, wherein one additional site is introduced at about position 30, 51, 57, 69, 88, 89, 136 or 138 and an N-linked carbohydrate chain is attached at said one additional site.

11. The analog of claim 10 wherein the one additional site is introduced at position 30.

12. The analog of claim 10 wherein the one additional site is introduced at position 51.

13. The analog of claim 10 wherein the one additional site is introduced at position 57.

14. The analog of claim 10 wherein the one additional site is introduced at position 69.

15. The analog of claim 10 wherein the one additional site is introduced at position 88.

16. The analog of claim 10 wherein the one additional site is introduced at position 89.

17. The analog of claim 10 wherein the one additional site is introduced at position 136.

18. The analog of claim 10 wherein the one additional site is introduced at position 138.

19. An analog of human erythropoietin comprising the amino acid sequence of human erythropoietin from residues 1–165 as shown in SEQ ID NO:26 except for one or more amino acid changes which provide for one or more additional glycosylation site(s) as compared to human erythropoietin, wherein one additional site is introduced at about position 123 or 125 and an O-linked carbohydrate chain is attached at said one additional site.

20. The analog of claim 19 wherein the one additional site is introduced at position 123.

21. The analog of claim 19 wherein the one additional site is introduced at position 125.

22. An analog of human erythropoietin comprising the amino acid sequence of human erythropoietin from residues 1–165 as shown in SEQ ID NO: 26 except for the amino acid changes selected from the group consisting of:

$Asn^{30}Thr^{32}$ EPO;
$Asn^{51}Thr^{53}$ EPO;
$Asn^{57}Thr^{59}$ EPO;
$Asn^{69}$EPO;
$Asn^{69}Thr^{71}$ EPO;
$Ser^{68}Asn^{69}Thr^{71}$ EPO;
$Val^{87}Asn^{88}Thr^{90}$ EPO;
$Ser^{87}Asn^{88}Thr^{90}$ EPO;
$Ser^{87}Asn^{88}Gly^{89}Thr^{90}$ EPO;
$Ser^{87}Asn^{88}Thr^{90}Thr^{92}$ EPO;
$Ser^{87}Asn^{88}Thr^{90}Ala^{162}$ EPO;
$Asn^{69}Thr^{71}Ser^{87}Asn^{88}Thr^{90}$ EPO;
$Asn^{89}Ile^{90}Thr^{91}$ EPO;
$Ser^{87}Asn^{89}Ile^{90}Thr^{91}$ EPO;
$Asn^{136}Thr^{138}$ EPO:
$Asn^{138}Thr^{140}$ EPO;
$Thr^{123}$ EPO;
$Thr^{125}$ EPO; and
$Pro^{124}Thr^{125}$ EPO.

23. An analog of human erythropoietin comprising the amino acid sequence of human erythropoietin from residues 1–165 as shown in SEQ ID NO: 26 except for the amino acid changes $Asn^{30}Thr^{32}Val^{87}Asn^{88}Thr^{90}$ EPO.

24. An analog of human erythropoietin comprising a fusion of a polypeptide fragment to the carboxy terminal end of human erythropoietin wherein the polypeptide fragment includes at least one glycosylation site having a carbohydrate chain attached thereto and wherein human erythropoietin comprises the amino acid sequence from residues 1–165 or 1–166 as shown in SEQ ID NO:26.

25. The analog of claim 24 wherein the polypeptide fragment is derived from the carboxy terminal end of human chorionic gonadotropin.

26. The analog of claim 25 wherein the polypeptide fragment has the amino acid sequence Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln (SEQ ID NO:25).

27. An analog of human erythropoietin having the in vivo biological activity of increasing hematocrit comprising an amino acid sequence which differs from the amino acid sequence of human erythropoietin from residues 1–165 or 1–166 as shown in SEQ ID NO:26 at least by having one or more additional glycosylation site(s) and having a carbohydrate chain attached to the additional site(s), wherein the analog is fused at its carboxy terminus to a polypeptide fragment having at least one glycosylation site with a carbohydrate chain attached thereto.

28. The analog of any of claims 10, 19, 22 or 23 fused at its carboxy terminus to a polypeptide fragment having at least one glycosylation site with a carbohydrate chain attached thereto.

29. The analog of claim 27 wherein the polypeptide fragment is fused to the carboxy terminal end of $Ser^{87}Asn^{88}Thr^{90}$ EPO.

30. The analog of claim 27 wherein the polypeptide fragment is fused to the carboxy terminal end of $Asn^{30}Thr^{32}Val^{87}Asn^{88}Thr^{90}$ EPO.

31. The analog of claim 27 wherein the polypeptide fragment is derived from the carboxy terminal end of human chorionic gonadotropin.

32. The analog of claim 27 wherein the polypeptide fragment has the amino acid sequence Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln (SEQ ID NO:25).

33. An analog of human erythropoietin having the in vivo biological activity of increasing hematocrit comprising an amino acid sequence which differs from the amino acid sequence of human erythropoietin from residues 1–165 as shown in SEQ ID NO:26 at least by having a deletion of one or more glycoyslation site(s) to which carbohydrate chains are attached and an addition of one or more non-naturally occurring glycosylation sites to which carbohydrate chains are attached to the additional site(s).

34. The analog of claim 33 comprising deletion of any of the N-linked carbohydrate sites in human erythropoietin and addition of an N-linked carbohydrate site at position 88.

35. The analog of claim 33 selected from the group consisting of:
$Gln^{24}Ser^{87}Asn^{88}Thr^{90}$ EPO;
$Gln^{38}Ser^{87}Asn^{88}Thr^{90}$ EPO; and
$Gln^{83}Ser^{87}Asn^{88}Thr^{90}$ EPO.

36. The analog of claims 10, 19, 22, 23, 24, 27 or 33 which is the product of expression of an exogenous DNA sequence.

37. A DNA sequence encoding an analog of human erythropoietin according to any of claims 10, 19, 22, 23, 24, 27 or 33.

38. A eucaryotic host cell transfected with a DNA sequence according to claim 37 in a manner allowing the host cell to express an analog of human erythropoietin.

39. A composition comprising an erythropoietin analog according to any of claims 10, 19, 22, 23, 24, 27 or 33 together with a pharmaceutically acceptable diluent, adjuvant or carrier.

40. A method of increasing hematocrit in a patient in need thereof comprising administering a therapeutically effective amount of the composition of claim 39.

* * * * *

UNITED STATES PATENT AND TRADEMARK OFFICE
CERTIFICATE OF CORRECTION

PATENT NO. : 7,217,689 B1 Page 1 of 1
APPLICATION NO. : 08/479892
DATED : May 15, 2007
INVENTOR(S) : Steven G. Elliott It is certified that error appears in the above-identified patent and that said Letters Patent is hereby corrected as shown below:

On the Title Page

Item (73), Assignee, "Amgen Inc., Thousand Oaks, CA (US)" should be --Kirin-Amgen Inc., Lucerne, Switzerland--.

Signed and Sealed this

Eighteenth Day of November, 2008

JON W. DUDAS
*Director of the United States Patent and Trademark Office*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CGCCCACCAA ACCTCAGCTG TGACAGCCGA                30

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

ATCTGTACAA CCGAAGCCTG GAGAGGT                27

(2) INFORMATION FOR SEQ ID NO:3:

(i) SEQUENCE CHARACTERISTICS:
      (A) LENGTH: 23 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGGCCTGGCC AACCTGTCGG AAG                                                 23

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TCCCCTCCAG ATAATGCCTC AGCTGC                                              26

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CAGATGCGAA CTCATCTGCT CCAC                                                24

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGGCCTGCAG GAATGGGAGC AGATGACCAG GTG                                      33

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TCCAGATGCG ACCTCAGCTG CTC                                                 23

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CCTCCAGATC CGACCTCAGC TGC                                    23

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GGGCCTGGCC AACCTGACAG AAGCTGTC                               28

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CAGGGCCTGT CCAACCTGAC AGAAGCTGTC                             30

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CAGATGCGAA CTCAACGGCT CCAC                                   24

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATGCGAACTC AACGGCTCCA CTCACAACAA TCACT                       35

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
CCAGATCCAA ATTCATCTGC TCCACTC                                          27
```

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
CCAGATCCAA ATTCAACAGC TCCACTC                                          27
```

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
CCAGATGCGA CAACAGCTGC TCCA                                             24
```

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
AGATCCGACC ACCGCTGCTC CAC                                              23
```

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
TGCTCCACTC ACAACAATCA CTG                                              23
```

(2) INFORMATION FOR SEQ ID NO:18:

(i) SEQUENCE CHARACTERISTICS:
        (A) LENGTH: 184 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
TCGAGGAACT GAAAAACCAG AAAGTTAACT GGTAAGTTTA GTCTTTTTGT CTTTTATTTC       60
AGGTCCCGGA TCCGGTGGTG GTGCAAATCA AGAACTGCT CCTCAGTGGA TGTTGCCTTT       120
```

ACTTCTAGGC CTGTACGGAA GTGTTACTTC TGCTCTAAAA GCTGCTGCAA CAAGCTGGTC    180

GACC    184

(2) INFORMATION FOR SEQ ID NO:19:

(i) SEQUENCE CHARACTERISTICS:
      (A) LENGTH: 107 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:19:

CCTGTAGGAC AGGGACAGA TCCTCTTCCT CAAAGGCCCC TCCCCCCAGC CTTCCAAGTC    60

CATCCCGACT CCCGGGGCCC TCGGACACCC CGATCCTCCC ACAATGA    107

(2) INFORMATION FOR SEQ ID NO:20:

(i) SEQUENCE CHARACTERISTICS:
      (A) LENGTH: 108 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:20:

GATCTCATTG TGGGAGGATC GGGGTGTCCG AGGGCCCCGG GAGTCGGGAT GGACTTGGAA    60

GGCTGGGGGG AGGGGCCGAG GAAGAGGATC TGTCCCCTGT CCTACAGG    108

(2) INFORMATION FOR SEQ ID NO:21:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:21:

GGAGGCCGAG CAGATCACGA CGG    23

(2) INFORMATION FOR SEQ ID NO:22:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:22:

CTTGAATGAG CAGATCACTG TCC    23

(2) INFORMATION FOR SEQ ID NO:23:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:23:

CTGTTGGTCC AGTCTTCCCA G                                                                                21

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

CCTGTTGGTC CAGTCTTCCC AGC                                                                              23

(2) INFORMATION FOR SEQ ID NO:25:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

(2) INFORMATION FOR SEQ ID NO:26:

(i) SEQUENCE CHARACTERISTICS:
        (A) LENGTH: 193 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..166

(ix) FEATURE:
        (A) NAME/KEY: Region
        (B) LOCATION: -27..0

(xi) SEQUENCE DESCRIPTION: SEQ ID NO:26:

Met Gly Val His Glu Cys Pro Ala Trp Leu Trp Leu Leu Leu Ser Leu
        -25                 -20                 -15

Leu Ser Leu Pro Leu Gly Leu Pro Val Leu Gly Ala Pro Pro Arg Leu
    -10                 -5                  1                   5

Ile Cys Asp Ser Arg Val Leu Glu Arg Tyr Leu Leu Glu Ala Lys Glu
                10                  15                  20

Ala Glu Asn Ile Thr Thr Gly Cys Ala Glu His Cys Ser Leu Asn Glu
                25                  30                  35

Asn Ile Thr Val Pro Asp Thr Lys Val Asn Phe Tyr Ala Trp Lys Arg
                40                  45                  50

Met Glu Val Gly Gln Gln Ala Val Glu Val Trp Gln Gly Leu Ala Leu
                55                  60                  65

Leu Ser Glu Ala Val Leu Arg Gly Gln Ala Leu Leu Val Asn Ser Ser
70                  75                  80                  85

-continued

```
Gln Pro Trp Glu Pro Leu Gln Leu His Val Asp Lys Ala Val Ser Gly
             90                      95                     100

Leu Arg Ser Leu Thr Thr Leu Leu Arg Ala Leu Gly Ala Gln Lys Glu
            105                     110                 115

Ala Ile Ser Pro Pro Asp Ala Ala Ser Ala Ala Pro Leu Arg Thr Ile
            120                 125                 130

Thr Ala Asp Thr Phe Arg Lys Leu Phe Arg Val Tyr Ser Asn Phe Leu
        135                 140                 145

Arg Gly Lys Leu Lys Leu Tyr Thr Gly Glu Ala Cys Arg Thr Gly Asp
150                 155                 160                 165

Arg
```